(12) United States Patent
Martin et al.

(10) Patent No.: US 11,578,348 B2
(45) Date of Patent: Feb. 14, 2023

(54) ENZYMATIC METHODS TO GENERATE HIGH YIELDS OF SEQUENCE SPECIFIC RNA WITH EXTREME PRECISION

(71) Applicant: The University of Massachusetts, Boston, MA (US)

(72) Inventors: Craig Martin, Amherst, MA (US); Elvan Cavac, Northampton, MA (US); Kithmie Harshana Malagodapathiranage, Amherst, MA (US); Shuo Sui, Sunderland, MA (US); Sarah L. Perry, Belchertown, MA (US); Yasaman Gholamalipour, Worcester, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 16/857,563

(22) Filed: Apr. 24, 2020

(65) Prior Publication Data

US 2020/0340028 A1 Oct. 29, 2020

Related U.S. Application Data

(60) Provisional application No. 62/933,119, filed on Nov. 8, 2019, provisional application No. 62/837,906, filed on Apr. 24, 2019.

(51) Int. Cl.
| | | |
|---|---|---|
| *C12P 19/34* | (2006.01) | |
| *C12N 9/12* | (2006.01) | |
| *C12N 15/10* | (2006.01) | |
| *C12Q 1/6865* | (2018.01) | |

(52) U.S. Cl.
CPC ............ *C12P 19/34* (2013.01); *C12N 9/1247* (2013.01); *C12N 15/10* (2013.01); *C12Q 1/6865* (2013.01)

(58) Field of Classification Search
None
See application file for complete search history.

(56) References Cited

U.S. PATENT DOCUMENTS

| | | |
|---|---|---|
| 8,101,385 B2 | 1/2012 | Cload et al. |
| 10,837,039 B2 * | 11/2020 | Wochner ............... C12Q 1/6844 |
| 2022/0112546 A1 | 4/2022 | Martin et al. |

FOREIGN PATENT DOCUMENTS

| | | | |
|---|---|---|---|
| WO | 2008078180 A2 | 7/2008 | |
| WO | WO-2019080704 A1 * | 5/2019 | ............... B01J 14/00 |

OTHER PUBLICATIONS

Alexopoulou, L. et al.; "Recognition of double-stranded RNA and activation of NF-κB by Toll-like receptor 3"; Nature, vol. 413, Issue No. 6857; 2001; pp. 732-738.
Arnaud-Barbe, N. et al.; "Transcription of RNA templates by T7 RNA polymerase by T7 RNA polymerase"; Nucleic Acids Research, vol. 26, Issue No. 15; 1998; pp. 3550-3554.
Baiersdorfer, M. et al.; "A facile method for removal of dsRNA contaminant from in vitro-transcribed mRNA"; Molecular Therapy Nucleic Acid, vol. 15; 2019; pp. 26-35.
Biebricher, C. K. et al.; "Template-free generation of RNA species that replicate with bacteriophage T7 RNA polymerase"; The EMBO Journal, vol. 15, Issue No. 13; 1996; pp. 3458-3465.
Cazenave, C. et al.; "RNA template-directed RNA synthesis by T7 RNA polymerase"; Proceedings of the National Academy of Sciences of the USA, vol. 91, Issue No. 15; 1994; pp. 6972-6976.
Donze, O. et al.; "RNA interference in mammalian cells using siRNAs synthesized with T7 RNA polymerase"; Nucleic Acids Research, vol. 30, Issue No. 10; 2002; pp. e-46-46; doi: 10.1093/nar/30.10.e46.
Dumousseau, M. et al.; "Melting, a flexible platform to predict the melting temperatures of nucleic acids"; BMC Bioinformatics, vol. 13: 101; doi: 10.1186/1471-2105-13-101.
Easton, L. E. et al.; "Rapid, nondenaturing RNA purification using weak anion-exchange fast performance liquid chromatography"; RNA, vol. 16, Issue No. 3; 2010; pp. 647-653.
Edelmann, F. T. et al.; "Production of pure and functional RNA for in vitro reconstitution experiments"; Methods, vol. 65, Issue No. 3; 2014; pp. 333-341.
Gong, P. et al.; "Initial bubble collapse plays a key role in the transition to elongation in T7 RNA polymerase"; The Journal of Biological Chemistry, vol. 279, Issue No. 43; 2004; pp. 44277-44285.
Hartmann, G.; "Nucleic Acid Immunity"; Advances in Immunology, vol. 133; 2017; pp. 121-169.
Kao, C. et al.; "A simple and efficient method to reduce nontemplated nucleotide addition at the 3 terminus of RNAs transcribed by T7 RNA polymerase"; RNA, vol. 5, Issue No. 9; 1999; pp. 1268-1272.
Kariko, K. et al.; "Generating the optimal mRNA for therapy: HPLC purification eliminates immune activation and improves translation of nucleoside-modified, protein-encoding mRNA"; Nucleic Acids Research, vol. 39, Issue No. 21; 2011; pp. e142-e142, doi: 10.1093/nar/gkr695.
Kauffman, K.J. et al.; "Efficacy and immunogenicity of unmodified and pseudouridine-modified mRNA delivered systemically with lipid nanoparticles in vivo"; Biomaterials, vol. 109; 2016; pp. 78-87.
Keefe, A. D. et al.; "Aptamers as therapeutics"; Nature Reviews. Drug Discovery, vol. 9, Issue No. 7; 2010; pp. 537-550.
Konarska, M. M. et al.; "Replication of RNA by the DNA-dependent RNA polymerase of phage T7"; Cell, vol. 57, Issue No. 8; 1989; pp. 423-431.

(Continued)

*Primary Examiner* — Celine X Qian
(74) *Attorney, Agent, or Firm* — Cantor Colburn LLP

(57) ABSTRACT

Described herein are synthetic methods for producing sequence-specific RNA oligonucleotides that eliminate impurities produced in prior art methods. In one aspect, an end-protected capture DNA complementary to a portion of the product RNA is employed. In another aspect, the template DNA is covalently or noncovalently linked to the RNA polymerase, either directly or through the use of a nontemplate DNA. In a third aspect, a flow chamber is employed. All of the methods can be used in combination.

18 Claims, 11 Drawing Sheets

Specification includes a Sequence Listing.

(56) References Cited

OTHER PUBLICATIONS

Konarska, M. M. et al.; "Structure of RNAs Replicated by the DNA-dependent T7 RNA Polymerase"; Cell, vol. 63, Issue No. 3; 1990; pp. 609-618.
Krupp, G. et al.; "Unusual promoter-independent transcription reactions with bacteriophage RNA polymerases" Nucleic Acids Research, vol. 17, Issue No. 8; 1989; pp. 3023-3036.
Krupp, G.; "RNA synthesis: strategies for the use of bacteriophage RNA polymerases"; Gene, vol. 72, Issue No. 1-2; 1988; pp. 75-89.
Krzyzosiak, W. et al.; "In vitro synthesis of 16S ribosomal RNA containing single base changes and assembly into a functional 30S ribosome"; Biochemistry, vol. 26, Issue No. 8; 1987; pp. 2353-2364.
Lemaire, P.A. et al.; "Mechanism of PKR Activation by dsRNA"; Journal of Molecular Biology, vol. 381, Issue No. 2; 2008; pp. 351-360.
Liu, C. et al.; "Fluorophore Labeling to Monitor tRNA Dynamics"; Methods in Enzymology, vol. 469; 2009; pp. 69-93.
Lukavsky, P. J. et al.; "Large-scale preparation and purification of polyacrylamide-free RNA oligonucleotides"; RNA, vol. 10, Issue No. 5; 2004; pp. 889-893.
Martin, C. T. et al.; "Processivity in Early Stages of Transcription by T7 RNA Polymerase"; Biochemistry, vol. 27, Issue No. 11; 1988; pp. 3966-3974.
Martins, R. et al.; "Ribonucleic acid purification"; Journal of Chromatography. A, vol. 1355; 2014; pp. 1-14.
Maslak, M. et al.; "Kinetic analysis of T7 RNA polymerase transcription initiation from promoters containing single-stranded regions"; Biochemistry, vol. 32, Issue No. 16; 1993; pp. 4281-4285.
McAllister, W. T.; "Structure and function of the bacteriophage T7 RNA polymerase (or, the virtues of simplicity)"; Cellular and Molecular Biology Research, vol. 39, Issue No. 4; 1993; pp. 385-391.
Mellits, K. H. et al.; "Removal of double-stranded contaminants from RNA transcripts: Synthesis of adenovirus Va RNA1 from a T7 vector"; Nucleic Acids Research, vol. 18, Issue No. 18; 1990; pp. 5401-5406.
Melton, D. A. et al.; "Efficient in vitro synthesis of biologically active RNA and RNA hybridization probes from plasmids containing a bacteriophage SP6 promoter"; Nucleic Acids Research, vol. 12, Issue No. 18; 1984; pp. 7035-7056.
Milligan, J. et al.; "Oligoribonucleotide synthesis using T7 RNA polymerase and synthetic DNA templates"; Nucleic Acids Research, vol. 15, Issue Nol. 21; 1987; pp. 8783-8798.
Milligan, J. et al.; "Synthesis of small RNAs using T7 RNA polymerase"; Methods in Enzymology, vol. 180; 1989; pp. 51-62.
Moroney, S. E. et al.; Abortive Products as Initiating Nucleotides during Transcription by T7 RNA Polymerase; Biochemistry, vol. 30, Issue No. 42; pp. 10343-10349.
Nacheva, G. A. et al.; "Preventing nondesired RNA-primed RNA extension catalyzed by T7 RNA polymerase"; European Journal of Biochemistry, vol. 270, Issue No. 7; 2003; pp. 1458-1465.
Ogawa, A.; "Rational design of artificial riboswitches based on ligand-dependent modulation of internal ribosome entry in wheat germ extract and their applications as label-free biosensors"; RNA, vol. 17, Issue No. 3; 2011; pp. 478-488.
Pichlmair, A. et al.; "Activation of MDA5 Requires Higher-Order RNA Structures Generated during Virus Infection"; Journal of Virology, vol. 83, Issue No. 20; 2009; pp. 10761-10769.
Rong, M. et al.; "Template strand switching by T7 RNA polymerase"; The Journal of Biological Chemistry, vol. 273, Issue No. 17; 1998; pp. 10253-10260.
Sahin, U. et al.; "mRNA-based therapeutics-developing a new class of drugs"; Nature Reviews. Drug Discovery, vol. 13, Issue No. 10; 2014; pp. 759-780.
Schlee, et al.; "Recognition of 5' Triphosphate by RIG-I Helicase Requires Short Blunt Double-Stranded RNA as Contained in Panhandle of Negative-Strand Virus"; Immunity, vol. 31, Issue No. 1; 2009; pp. 25-34.
Schneider, C. A. et al.; "NIH Image to ImageJ: 25 years of image analysis"; Nature Methods, vol. 9, Issue No. 7; 2012; pp. 671-675.
Sherlin, L. D. et al.; "Chemical and enzymatic synthesis of tRNAs for high-throughput crystallization"; RNA, vol. 7, Issue No. 11; 2001; pp. 1671-1678.
Sousa, R.;"T7 RNA Polymerase"; Encyclopedia of Biological Chemistry: Second Edition; Academic Press; 2013; pp. 355-359.
Sultana, S. et al.; "Transcriptional fidelities of human mitochondrial POLRMT, yeast mitochondrial Rpo41, and phage T7 single-subunit RNA polymerases"; The Journal of Biological Chemistry, vol. 292, Issue No. 44; 2017; pp. 18145-18160.
Tycowski, K. T. et al.; "Modification of U6 spliceosomal RNA is guided by other small RNAs"; Molecular Cell, vol. 2, Issue No. 5; 1998; pp. 629-638.
Uhm, H. et al.; "Single-molecule FRET studies on the cotranscriptional folding of a thiamine pyrophosphate riboswitch"; Proceedings of the National Academy of Sciences of the USA; vol. 115, Issue No. 2; 2018; pp. 331-336.
Weissman, D. et al.; "HPLC purification of in vitro transcribed long RNA"; Methods in Molecular Biology, vol. 969; 2013; pp. 43-54.
Wienert, B. et al.; "In vitro-transcribed guide RNAs trigger an innate immune response via the RIG-I pathway"; PLoS Biology, vol. 16, Issue No. 7; 2018; e2005840, doi: 10.1371/journal.pbio.2005840.
Zaher, H. S. et al.; "RNA polymerase mediates fast promoter-independent extension of unstable nucleic acid complexes"; Biochemistry, vol. 43, Issue No. 24; 2004; pp. 7873-7880.
Bosnes et al.; "Solid-phase In Vitro Transcription and mRNA Purification Using Dynabeads, Superparamagnetic Beads"; A Poster Presented at 5th International mRNA Health Conference; Nov. 2017; DOI:10.13140/RG.2.2.11334.16962.
Esposito et al.; "Cross-linking of promoter DNA to T7 RNA polymerase does not prevent formation of a stable elongation complex"; The Journal of Biological Chemistry, vol. 279, Issue No. 43; 2004; pp. 44270-44276.
Gholamalipour et al.; "3' end additions by T7 RNA polymerase are RNA self-templated, distributive and diverse in character-RNA-Seq analyses"; Nucleic Acids Research, vol. 46, Issue No. 18; 2018; pp. 9253-9263.
Gholamalipour et al.; "Efficient inhibition of RNA self-primed extension by addition of competing 3'-capture DNA-improved RNA synthesis by T7 RNA polymerase"; Nucleic Acids Research, vol. 47, Issue No. 19; 2019; e118. doi: 10.1093/nar/gkz700; 7 pages.
Triana-Alonso et al.; "Self-coded 3'-extension of run-off transcripts produces aberrant products during in vitro transcription with T7 RNA polymerase"; The Journal of Biological Chemistry, vol. 270, Issue No. 11; 1995; pp. 6298-6307.
Vestheim et al.; "Application of blocking oligonucleotides to improve signal-to-noise ratio in a PCR"; Methods in Molecular Biology, vol. 687; 2011; pp. 265-274.
Sarcar, S. N. et al.; "A specific, promoter-independent activity of T7 RNA polymerase suggests a general model for DNN/RNA editing in single subunit RNA Polymerases"; Scientific Reports, vol. 8, Article 13885; 2018; doi: https://doi.org/10.1038/s41598-018-32231-6.

* cited by examiner

ENZYMATIC METHODS TO GENERATE HIGH YIELDS OF SEQUENCE SPECIFIC RNA WITH EXTREME PRECISION

CROSS-REFERENCE TO RELATED APPLICATIONS

This application claims priority to U.S. Provisional Application 62/837,906 filed on Apr. 24, 2019, and U.S. Provisional Application 62/933,119, filed on Nov. 8, 2019, which are incorporated herein by reference in their entirety.

STATEMENT REGARDING FEDERALLY SPONSORED RESEARCH & DEVELOPMENT

This invention was made with government support under MCB-1516896 awarded by the National Science Foundation. The government has certain rights in the invention.

INCORPORATION-BY-REFERENCE OF MATERIAL SUBMITTED ELECTRONICALLY

Incorporated by reference in its entirety herein is a computer-readable nucleotide listing submitted concurrently herewith and identified as follows: one 3,058 Byte ASCII (Text) file named "Sequence List TEXT version UMA0129US3 (UMA 19-035 thru 19-037, 19-037.1, 20-014)," created on Apr. 22, 2020

FIELD OF THE DISCLOSURE

The present disclosure is related to novel enzymatic methods of synthesizing product RNAs which reduce double stranded impurities produced in prior methods.

BACKGROUND

The 21$^{st}$ century is seeing huge advances in RNA biology and biochemistry. These studies require pure, monodisperse preparations of RNA. In RNA applications, mRNA therapeutics are poised to become a major player in biologic pharmaceuticals, an already large, established, and growing field (indeed, it is argued that RNA biologics will largely replace protein biologics). The main challenge holding back applications is that the mRNA often triggers the innate immune response in patients, a potentially lethal outcome. It is well known that human cells have an innate immune response that responds to the presence of double stranded RNA (which the mRNA should not be, in theory).

RNA therapeutics approaches are hampered by an undesired immune response that has led to dramatic failures in clinical trials (including some patient deaths). Various companies have developed technologies built on the incorporation of base analogs into the RNA. Success with this approach has been promising, but limited. Indeed, mRNA drugs in clinical trials are vaccines, exploiting the immune response as an adjuvant. Their original target, gene replacement therapies, continue to languish, as extensive purification only sometimes alleviates this problem, and not fully.

Currently, there are two established routes to generate synthetic RNA: chemically or enzymatically. The chemical route is generally limited to RNAs shorter than about 30-50 bases in length, depending on the application. The enzymatic route is routinely used to generate large quantities of short (e.g., 30 base) and long (kilobase) RNA in vitro using T7 RNA polymerase (T7RP) or one of its closely related family members. T7RP is a promoter specific, highly processive enzyme. However, it also participates in promoter-independent transcription that results in unwanted product. This promiscuity often contaminates the transcription pool with undesired longer (and shorter) products. It is believed to be longer, double stranded impurities in the RNA that present the biggest challenge to the RNA therapeutics industry, as delivered RNAs often invoke an unwanted innate immune response (which has led to patient deaths in clinical trials).

What is needed are novel synthetic methods for sequence-specific RNA oligonucleotides that eliminate impurities produced in prior art methods.

BRIEF SUMMARY

In an aspect, a method of synthesizing a product RNA comprises preparing a reaction mixture comprising a functional template DNA for the product RNA, an RNA polymerase and a capture DNA under conditions for product RNA synthesis, synthesizing the product RNA in the reaction mixture, optionally removing the capture DNA after product RNA synthesis, and optionally purifying the product RNA, wherein the capture DNA is 3' end protected, and is complementary to 8 to 20, preferably 12 to 20 nucleotides at the 3' end of the product RNA, and wherein the functional template DNA, the RNA polymerase, capture DNA or a combination thereof, is optionally covalently or noncovalently attached to one or more solid supports.

In another aspect, a method of synthesizing a product RNA comprises preparing a reaction mixture comprising a functional template DNA for the product RNA and an RNA polymerase under conditions for RNA synthesis, wherein the RNA polymerase is covalently or noncovalently linked to the functional template DNA in a manner that allows for synthesis of the product RNA, synthesizing the product RNA in the reaction mixture, and optionally purifying the product RNA, wherein the functional template DNA, the RNA polymerase, or both, is optionally covalently or noncovalently attached to a solid support.

In another aspect, a method of synthesizing a product RNA comprises preparing a reaction mixture comprising a functional template DNA for the product RNA, and an RNA polymerase under conditions for RNA synthesis, wherein the RNA polymerase is covalently or noncovalently linked to a nontemplate DNA that is 10 to 10,000 nucleotides or longer in length, and wherein the nontemplate DNA is complementary to a minimum of 10 nucleotides of the template DNA upstream of the transcription start site, or wherein the nontemplate DNA is complementary to all or part of the entire template strand DNA in its coding region, synthesizing the product RNA in the reaction mixture, and optionally purifying the product RNA, wherein the template DNA, the nontemplate, the RNA polymerase, or a combination thereof, is optionally covalently or noncovalently attached to a solid support.

In yet another aspect, a method of synthesizing a product RNA comprises (i) preparing a reaction mixture comprising a functional template DNA for the product RNA, and an RNA polymerase under conditions for RNA synthesis, wherein functional template DNA and the RNA polymerase are immobilized to a solid support, and wherein the contacting is done in a flow chamber, synthesizing the product RNA in the reaction mixture and continuously removing the product RNA from the flow chamber while flowing fresh RNA synthesis reagents into the flow chamber, and optionally purifying the product RNA, or (ii) preparing a reaction mixture comprising a functional template DNA for the product RNA, and an RNA polymerase under conditions for RNA synthesis, wherein the RNA polymerase is covalently or noncovalently linked to a nontemplate DNA that is 10 to 10,000 nucleotides or longer in length, and wherein the nontemplate DNA is complementary to a minimum of 10 nucleotides of the template DNA upstream of the transcription start site, or wherein the nontemplate DNA is complementary to all or part of the entire template strand DNA in the coding region, wherein the nontemplate DNA and the RNA polymerase are immobilized to a solid support, and wherein the contacting is done in a flow chamber, synthesizing the product RNA and continuously removing the product RNA from the flow chamber while flowing fresh RNA synthesis reagents into the flow chamber, and optionally purifying the product RNA.

In another aspect, a method of providing a modified, amplified functional template DNA comprises providing a starting functional template DNA and an amplification primer, the amplification primer comprising one or more deoxyuridines on the nontemplate strand, under conditions for DNA amplification, amplifying the starting DNA functional template to provide an amplified DNA functional template, and excising the deoxyuridines from the amplification primer to provide the modified, amplified functional template DNA.

In a yet further aspect, a method of purifying a product RNA, comprises adding a capture DNA to a reaction mixture for producing the product RNA, the reaction mixture comprising the product RNA, a functional template DNA for the product RNA, and an RNA polymerase under conditions for RNA synthesis; wherein the capture DNA is 10 nucleotides or longer in length, and wherein the capture DNA comprises a capture sequence complementary to a minimum of 10 nucleotides of the 3' terminus of the product RNA, and wherein the capture DNA is tethered to a solid support;

incubating the tethered capture DNA and the reaction mixture to provide binding of the capture DNA and the product RNA, washing to remove unbound reaction components, and eluting the product RNA from the tethered capture DNA.

BRIEF DESCRIPTION OF THE DRAWINGS

FIG. 2A shows self-primed extension reaction of synthetic RNA. FIG. 2B shows denaturing (20% urea) gel electrophoretic analysis: radiolabeled 24-base synthetic RNA was reacted with T7 RNA polymerase for 0 min, 5 min and 4 h, in the absence (−) or presence (+) of capture DNA. FIG. 2C shows that DNA captures the 3' end of the RNA, competing with self-primed extension.

FIG. 4A shows encoded RNAs and corresponding capture DNAs. FIG. 4B shows denaturing (20% urea) gel analysis of 4 h high yield transcription reactions. Transcripts were labeled by [$\alpha$-$^{32}$P] ATP. Lanes "24" above demonstrate clearly that Capture-17 inhibits formation of primer extended products. Lanes "24Alt" show that for an RNA sequence that does not promote self-primed extension, the presence of Capture-17 has no effect. Finally, lanes "34" show that the effect is not dependent on the length of the RNA and that self-primed extension proceeds farther on longer RNAs.

FIG. 5A shows high yield transcription reaction (4 h) for RNA-24 in the presence of varying concentrations of complementary capture DNA (Capture-17). FIG. 5B shows time dependence of transcription reaction products in the presence (+) or absence (−) of 200 µM capture DNA.

FIG. 7A shows site-specific coupling of nontemplate DNA to protein generates a "universal reagent," to which template DNA of arbitrary RNA sequence can be added to generate a functional template encoding that RNA sequence. FIG. 7B shows to prevent primer extension reactions, salt was added, as indicated, to each reaction prior to initiation of high yield transcription (3 hrs, 7.5 mM each substrate NTP). The crosslinked species generates substantially more pure, desired RNA. Note that this gel uses staining for detection, so the DNA template and nontemplate strands are also present, as marked.

FIG. 9A shows salt dependence of transcription profiles for tethered and untethered complexes analyzed by 20%, 7M urea denaturing gel electrophoresis, labeled via incorporation of [$\alpha$-$^{32}$P] ATP. The final concentrations NaCl added (to the standard reaction mixture) are shown. FIG. 9B shows quantification of individual gel lanes in 9A.

FIG. 10A shows the salt dependence of transcription profiles for tethered and untethered complexes encoding RNA-24Alt, analyzed as in FIG. 2. FIG. 10B shows the quantification of individual lanes in FIG. 10A.

FIG. 11A shows the low and high salt transcription profiles for tethered and untethered complexes analyzed as in FIG. 9. FIG. 11B shows gel quantification of FIG. 11A.

FIG. 12A shows a summary of the repeated reaction cycle. FIG. 12B shows a low (0 M) and high (0.4 M) added NaCl transcription profiles for untethered and tethered transcription of RNA-24Alt analyzed as in FIG. 10. After "Use 1" the reaction solution was removed, beads washed, and a new substrate NTP solution was added to initiate "Use 2" (with the same cycle subsequently used to initiate "Use 3"). FIG. 12C shows gel quantification of the individual lanes in 10B.

FIG. 13A displays a diagram of a reactor in current development, shown in FIG. 13D. The precise nature of the coupling shown in FIG. 13B is likely not important. The inset FIG. 13C shows actual beads (not yet carrying RNA polymerase) being held in place by flow against a designed, physical barrier. The design in FIG. 13E is a simple extension of FIG. 13A, including a chamber with beads containing 3'-capture DNA (or with an affinity tag to bind 3' capture DNA flowing continuously).

FIG. 17A shows covalent attachment of the nontemplate DNA to a Halo-Tag® domain fused to the polymerase generates a "universal reagent." Users provide template DNA encoding RNA of interest.

FIG. 17B illustrates for long (e.g., mRNA) RNA, a Br-modified DNA duplex can be generated (via PCR), and then (covalently) bound to Halo-T7RP as above.

As shown in FIG. 20A, linear DNA containing the reverse complement (capture DNA) of the 3'product RNA sequence is ligated to form a circular DNA functional template. A primer is then extended using a strand displacing DNA polymerase to generate a long capture DNA containing repetitions of the capture sequence. As shown in FIG. 20B, the RCA construct can dramatically increase the capacity of any immobilization system. As shown in FIG. 20C, an RCA primer can attach to solid support for purification via a variety of means:

FIG. 21A shows capture DNA circularized with ligase (either with or without a "splint" DNA to aid circularization). dT25 DNA is covalently attached to beads is then used to prime rolling circle amplification. The product is capture DNA covalently attached to magnetic beads that contains many target sites for purification. FIG. 21B shows the resulting bead-capture DNA conjugate is then used as in the method of FIG. 19 to purify only correct length RNA.

The above-described and other features will be appreciated and understood by those skilled in the art from the following detailed description, drawings, and appended claims.

DETAILED DESCRIPTION

Figure 1:
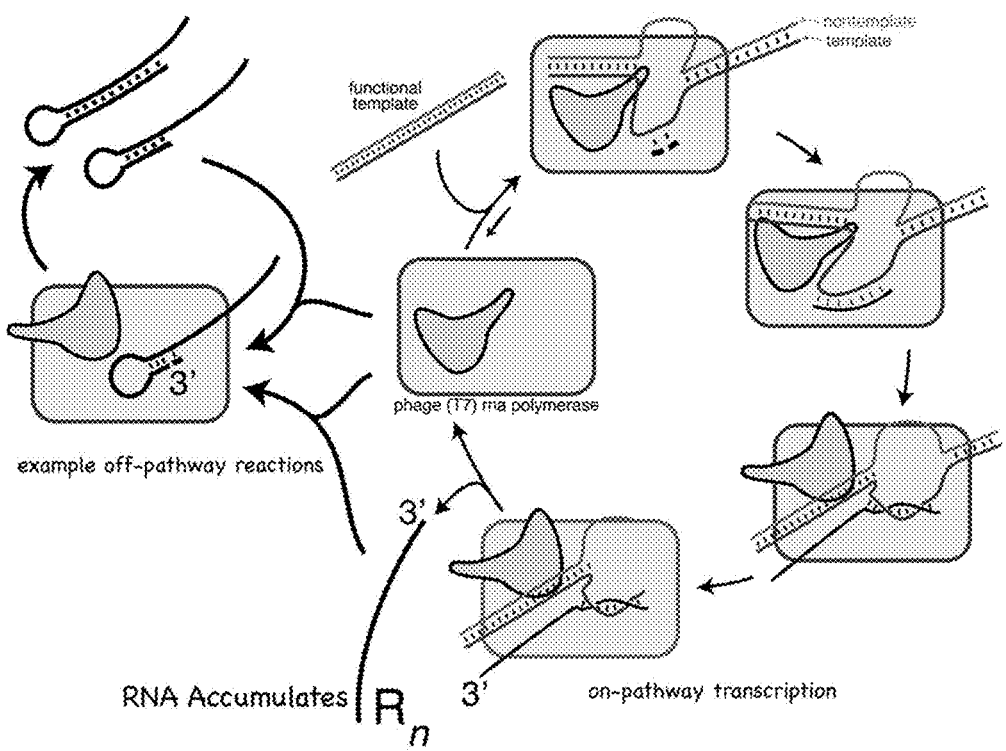
FIG. 1 shows high yield transcription favors impurities. On-pathway synthesis (and accumulation of large concentrations) of desired RNA ($R_n$) drives off-pathway primer extension that generates heterogeneous, double stranded impurities.

As illustrated in FIG. 1, under the current high yield synthesis conditions used in the production of mRNA, a side reaction, in which RNA polymerase binds and extends the accumulating product RNA, turns the correct RNA (or other RNAs) into double stranded RNA (dsRNA). Without being held to theory, it is believed that this dsRNA is the primary source of the immune responses that have been observed in RNA therapy. Pseudouridine reduces primer extension, explaining the utility of modified nucleotides in synthesis, fully consistent with FIG. 1.

Based upon this understanding of how dsRNA is made under high yield conditions, the inventors have developed multiple approaches to reducing dsRNA synthesis from the outset. The underlying principle is to prevent re-binding of the correct length RNA to the polymerase, preventing its extension to the double stranded form. All of the methods described herein are complementary to the use of modified nucleotides.

Some definitions are provided.

The term "polynucleotide" is interchangeable with nucleic acid and includes any compound and/or substance that comprise a polymer of nucleotides. RNA transcript products produced by the methods described herein and functional templates DNA used in the methods are polynucleotides. Exemplary polynucleotides include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof. Polynucleotides may include naturally occurring nucleotides as well as modified nucleotides such as pseudouridine 1-N-pseudouridine, dye-labeled nucleotides, biotin-labeled nucleotide, and others.

As used herein, an "RNA transcript" or "product RNA" refers to a ribonucleic acid produced by an in vitro transcription reaction using a DNA functional template and an RNA polymerase. The RNA transcript can include modifications, e.g., modified nucleotides. Product RNAs can have lengths of 10 to greater than 5,000 and include, for example, mRNAs.

A DNA "functional template" refers to a polynucleotide template for RNA polymerase. Typically, functional template DNA includes the sequence coding for a product RNA of interest operably linked to a fully or partially double stranded RNA polymerase promoter sequence.

"Operably linked" refers to a functional connection between two or more molecules, constructs, transcripts, entities, moieties or the like. For example, a coding sequence for a product RNA operably linked to an RNA polymerase promoter allows transcription of the product RNA.

Any number of RNA polymerases or variants may be used in the methods described herein. The polymerase may be selected from, but is not limited to, a phage RNA polymerase, e.g., a T7 RNA polymerase, a T3 RNA polymerase, an SP6 RNA polymerase, a K11 RNA polymerase, and/or mutant polymerases such as, but not limited to, polymerases able to incorporate modified nucleic acids, polymerases showing reduced abortive cycling, and polymerases with increased thermostability. As used herein, the terms a T7 RNA polymerase, a T3 RNA polymerase, a K11RNA polymerase, and an SP6 RNA polymerase include both wild type, mutant and truncated polymerases, so long as RNA polymerase activity is maintained.

RNA polymerases may be modified by inserting or deleting amino acids of the RNA polymerase sequence. As a non-limiting example, the RNA polymerase may be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties). Variants may be obtained by evolving an RNA polymerase, optimizing the RNA polymerase amino acid and/or nucleic acid sequence and/or by using other methods known in the art.

"Conditions for product RNA synthesis" are in vitro transcription conditions. Such conditions comprise a transcription buffer, nucleotide triphosphates (NTPs), optionally an RNase inhibitor and an RNA polymerase. The NTPs may be selected from, but are not limited to, those described herein including natural and unnatural (modified) NTPs.

An exemplary in vitro transcription reaction includes the following: an RNA polymerase, e.g., a T7 RNA polymerase at a final concentration of, e.g., 1000-12000 U/mL, e.g., 7000 U/mL; the DNA functional template at a final concentration of, e.g., 10-70 nM, e.g., 40 nM; nucleotides (NTPs) at a final concentration of e.g., 0.5-10 nM, e.g., 7.5 nM each; magnesium at a final concentration of, e.g., 12-60 mM, e.g., magnesium acetate at 40 mM; a buffer such as, e.g., HEPES or Tris at a pH of, e.g., 7-8.5, e.g. 40 mM Tris HCl, pH 8

In some embodiments, 5 mM dithiothreitol (DTT) and/or 1 mM spermidine is included in the transcription reaction. In some embodiments, an RNase inhibitor is included in the in vitro transcription reaction to ensure no RNase induced degradation during the transcription reaction. For example, murine RNase inhibitor can be utilized at a final concentration of 1000 U/mL. In some embodiments, a pyrophosphatase is included in the in vitro transcription reaction to cleave the inorganic pyrophosphate generated following each nucleotide incorporation into two units of inorganic phosphate. This ensures that magnesium, which is essential for transcription, remains in solution and does not precipitate as magnesium pyrophosphate. For example, an *E. coli* inorganic pyrophosphatase can be utilized at a final concentration of 1 U/mL.

The in vitro transcription reaction can be allowed to proceed, for example, under constant mixing at 37° C. for 1-12 hours. Typical yields can be, e.g., 5 mg of RNA per mL of transcription reaction.

In an aspect, a method of synthesizing a product RNA comprises
preparing a reaction mixture comprising a functional template DNA for the product RNA, an RNA polymerase and a capture DNA under conditions for product RNA synthesis,
synthesizing the product RNA in the reaction mixture,
optionally removing the capture DNA after product RNA synthesis, and
optionally purifying the product RNA, wherein the capture DNA is 3' end protected, and is complementary to 8 to 20 or more, preferably 12 to 20 nucleotides or more at the 3' end of the product RNA, and
wherein the functional template DNA, the RNA polymerase, the capture DNA or a combination thereof, is optionally covalently or noncovalently attached to one or more solid supports.

The approach involves carrying out in vitro transcription in the presence of a 3'-end protected capture DNA oligonucleotide. The minimum length of the portion of the capture DNA that is complementary to the 3' end of the product RNA is determined by stability. The use of modified nucleotides can increase stability at shorter lengths. In general, the overall length of the capture DNA is not critical so long as the complementary region has sufficient length to complex with the 3' end of the product RNA. Thus, the capture DNA may be longer than the region that is complementary to the 3' end of the product RNA.

This method dramatically favors correct, promoter-dependent transcription and prevents promiscuous promoter-independent activities. Using the capture DNA method, high yields of pure runoff RNA of various sizes can be produced. The method is tested to be superior to the traditional RNA synthesis methods (both synthetic and enzymatic) in terms of quality, scale, speed and price. The method has been compared with the commonly used HiScribe™ T7 High Yield RNA synthesis kit (New England Biolabs) and the capture DNA method was shown to be far superior in terms of quality and purity, as assayed by gel electrophoresis, while being comparable in scale, speed and price. The capture DNA method is complementary to the use of HiScribe™.

The functional template DNA, the RNA polymerase, the capture DNA or a combination thereof, is optionally covalently or noncovalently attached to one or more solid supports. In an aspect, the capture DNA and the functional template DNA and/or RNA polymerase are on separate supports, although it is possible for them to be linked to the same support.

Exemplary groups for 3' end-protection of the capture DNA include 3' amino, 3'-deoxy (H), 3'-phosphorylation, 3'-O-methyl, 3'-fluorophore, 3'-biotin, 3'-azide, 3'-fluoro, 3'-PEG, 3'-mismatched bases, and any modification that is inconsistent with the native phosphoryl transfer function of an RNA polymerase.

In an aspect, the capture DNA is removed by elevated temperature, DNase, or toehold-mediated strand displacement, for example.

In an aspect, the RNA is purified using commercially available kits such as the Ambion/Applied Biosystems (Austin, Tex.) MEGAClear RNA™.

In an aspect, the RNA polymerase is covalently or non-covalently linked to the functional template DNA, wherein the noncovalent linking allows for synthesis of the product RNA.

In a specific aspect, the RNA polymerase is covalently or noncovalently linked to a nontemplate DNA that is 10 to 10,000 nucleotides or longer in length, and wherein the nontemplate DNA is complementary to a minimum of 10, 14, preferably 17 nucleotides of the template DNA upstream of the transcription start site, or wherein the nontemplate DNA is complementary to all or part of the entire template strand DNA in the coding region. The nontemplate DNA noncovalently links the RNA polymerase to the template DNA by essentially acting as an intermediary between the RNA polymerase and the template DNA.

In another aspect, a method of synthesizing a product RNA comprises preparing a reaction mixture comprising a functional template DNA for the product RNA, and an RNA polymerase under conditions for RNA synthesis, wherein the RNA polymerase is covalently or noncovalently linked to the functional template DNA, wherein the linking allows for synthesis of the product RNA, synthesizing the product RNA in the reaction mixture, and optionally purifying the product RNA, wherein the functional template DNA, the RNA polymerase, or both, is optionally covalently or noncovalently attached to a solid support.

In an aspect, the template DNA is also covalently or noncovalently linked to the RNA polymerase by a means additional to the nontemplate DNA.

Figure 16:
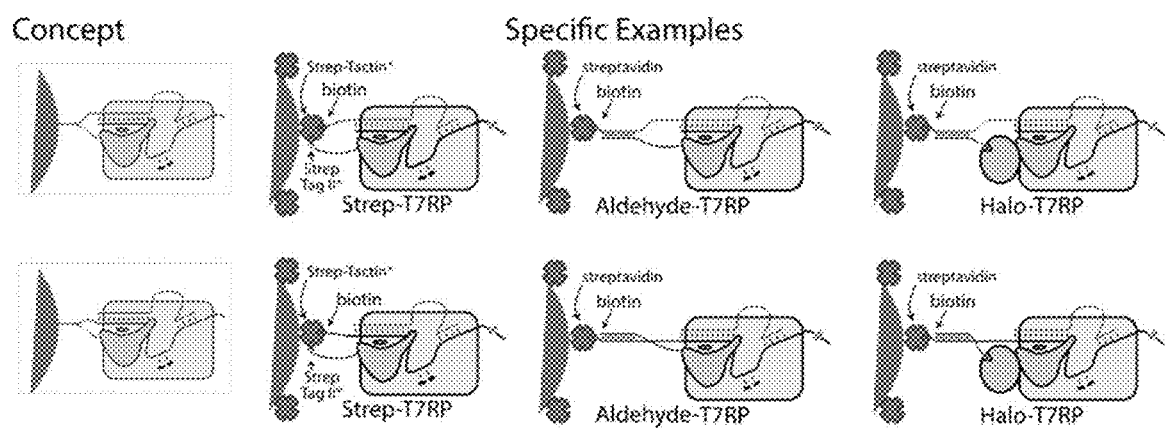
FIG. 16 illustrates additional methods for coupling an RNA polymerase to a functional template DNA.
Figure 17:
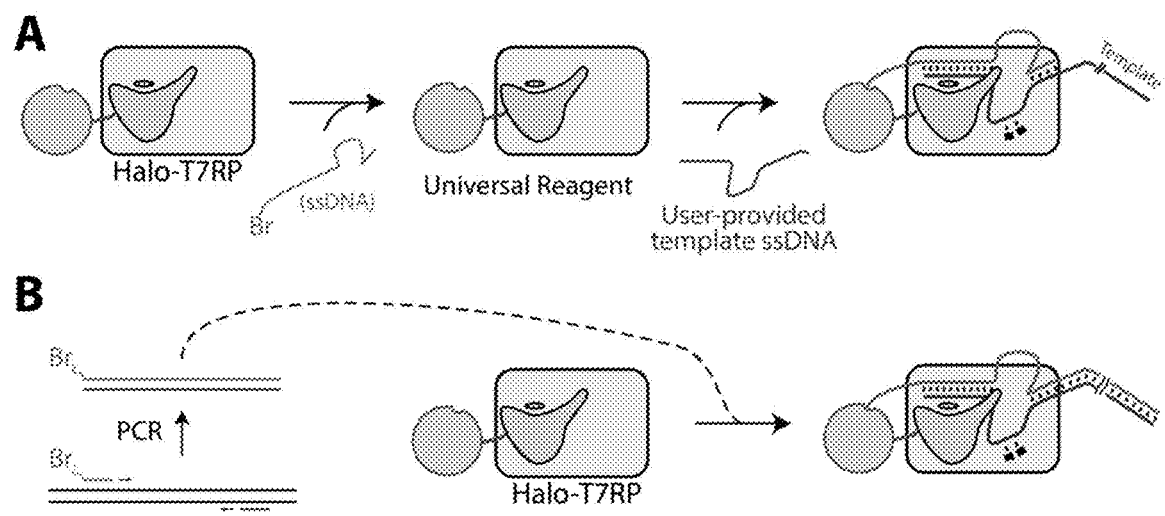
FIG. 17 illustrates alternate tethering schemes.

The template DNA can be linked to the polymerase by using 3' modifications that parallel the 5' modifications described herein. FIGS. 16 and 17 illustrate additional options for linking RNA polymerase to template and/or nontemplate DNA such as using a T7 RNA polymerase variant containing an N-terminal Strep-tag® II peptide and a biotin labeled DNA template; using an aldehyde labeled T7 RNA polymerase and a biotin labeled DNA functional template; or using a halo labeled T7 RNA polymerase and a biotin labeled DNA functional template.

In another aspect a method of synthesizing a product RNA comprises preparing a reaction mixture comprising a functional template DNA for the product RNA, and an RNA polymerase under conditions for RNA synthesis, wherein the RNA polymerase is covalently or noncovalently linked to a nontemplate DNA that is 10 to 10,000 nucleotides or longer in length, and wherein the nontemplate DNA is complementary to a minimum of 10 nucleotides of the template DNA upstream of the transcription start site, or wherein the nontemplate DNA is complementary to all or part of the entire template strand DNA in the coding region, synthesizing the product RNA, and optionally purifying the product RNA, wherein the template DNA, the nontemplate, the RNA polymerase, or a combination thereof, is optionally covalently or noncovalently attached to a solid support.

In this aspect, the nontemplate DNA noncovalently links the RNA polymerase to the template DNA by essentially acting as an intermediary between the RNA polymerase and the template for the RNA.

The methods include, for example, tethering template or nontemplate DNA and RNA polymerase to a solid support, or alternatively, simply to each other, and then optionally carrying out transcription at elevated salt concentrations. Elevated salt weakens the product re-binding that leads to longer, double stranded products. Tethering RNA polymerase and template DNA together, either directly or through a nontemplate DNA, allows the polymerase to function at these high salt concentrations. This method dramatically favors correct, promoter-dependent transcription and prevents promiscuous promoter-independent activities. The method can be used to synthesize high yields of pure runoff RNA of various sizes. The method has been compared side by side with the commonly used HiScribe™ T7 High Yield RNA synthesis kit (New England Biolabs) and was shown to be far superior in terms of quality and purity, as assayed by gel electrophoresis, while being comparable in scale, speed and price.

The template or nontemplate DNA and the RNA polymerase can be linked using a variety of bioconjugation chemistries such as those using amine, acid, hydrazine, aldehyde/ketone, hydroxylamine, maleimide/alkylhalide and sulfhydryl functional groups.

In an aspect, the RNA polymerase comprises a sequence for a formyl glycine generating enzyme, and the template or nontemplate DNA comprises a 5' hydrazine which is covalently coupled to an aldehyde in the RNA polymerase.

In another aspect, the RNA polymerase comprises an avidin-binding peptide, the template or nontemplate DNA comprises a 5'biotin label, and the RNA polymerase is noncovalently linked to the template or nontemplate DNA via beads that bind both the avidin-binding peptide and the biotin.

An advantage of linking the RNA polymerase and the template DNA, either directly or through for example a nontemplate DNA, is that high salt conditions may be used for RNA production as well as low salt conditions. As used herein, high salt conditions are 50 to 1000 mM, preferably 100 to 500 mM. When a nontemplate DNA is employed, the nontemplate DNA acts as an agent that brings together the RNA polymerase and the template DNA. The nontemplate DNA also allows formation of the template-nontemplate duplex promoter sequence that is critical for binding in an initiation competent state.

In an aspect, the nontemplate DNA may include a tag, such as an affinity purification tag, such as biotin which binds to a streptavidin column.

In an aspect, the wherein contacting can further includes a capture DNA as described above in the first aspect.

In the foregoing aspects, the template DNA, the nontemplate DNA or the RNA polymerase, or all three, can be covalently or noncovalently attached to a solid support such as a bead via a linker or chemical moiety such as a polyethylene glycol linker. Exemplary solid supports include beads such as magnetic beads.

In another aspect, a method of synthesizing a product RNA comprises (i) preparing a reaction mixture comprising a functional template DNA for the product RNA, and an RNA polymerase under conditions for RNA synthesis, wherein the functional template DNA and the RNA polymerase are immobilized, e.g., tethered to a solid support, and wherein the contacting is done in a flow chamber, synthesizing the product RNA and continuously removing the product RNA from the flow chamber while flowing fresh RNA synthesis reagents into the flow chamber, and optionally purifying the product RNA, or (ii) preparing a reaction mixture comprising a functional template DNA for the product RNA, and an RNA polymerase under conditions for RNA synthesis, wherein the RNA polymerase is covalently or noncovalently linked to a nontemplate DNA that is 10 to 10,000 nucleotides or longer in length, and wherein the nontemplate DNA is complementary to a minimum of 10, 14, preferably 17 nucleotides of the template DNA upstream of the transcription start site, or wherein the nontemplate DNA is complementary to all or part of the entire template strand DNA in the coding region, wherein the nontemplate DNA and the RNA polymerase are immobilized to a solid support, and wherein the contacting is done in a flow chamber, synthesizing the product RNA and continuously removing the product RNA from the flow chamber while flowing fresh RNA synthesis reagents into the flow chamber, and optionally purifying the product RNA.

The approach involves tethering functional template DNA and RNA polymerase to a solid support such as a bead, and then carrying out transcription in a fluidics (flow) reactor, where product is continuously removed from the reactor, while fresh RNA synthesis reagents are flowed in. This process can be done under normal or elevated salt concentrations. This method should dramatically favor correct, promoter-dependent transcription and prevent promiscuous promoter-independent activities. This method will allow for the production of high yields of pure runoff RNA of various sizes.

Figure 11:
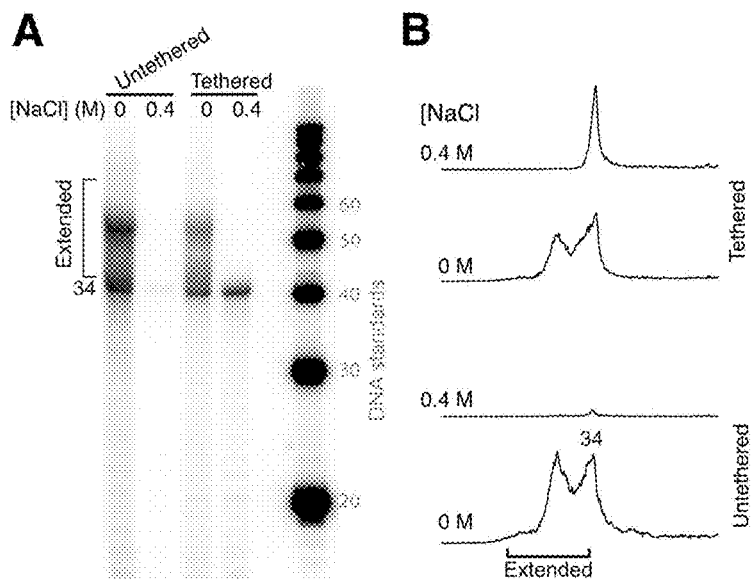
FIG. 11 shows Improvements are independent of RNA length.

Exemplary solid supports include microparticles and beads, for example. Enzyme and DNA can be attached to the beads via a variety of protocols (see above). In production, a complete system would comprise a multiple use device to deliver fluidics, mating with disposable "chips" on which the reaction is carried out. The device contains pumps, valves and automation to control flow rates and [optionally] delivered reagent concentrations. The disposable chip contains fluidics paths that encompass the reaction chamber, with or without pre-loaded bead-enzyme constructs onto which the desired functional template would attach (under setup flow). The chip mates appropriately with the device for flow. FIG. 11 shows the initial prototype, alongside an example production device. Variants can drive multiple chips in parallel, for higher throughput. Device/chip systems can be produced at different scales, to accommodate desired RNA synthesis yields.

In an aspect, the flow chamber is in operable communication with a downstream chamber comprising an immobilized reagent that specifically binds full-length product RNA, wherein the immobilized reagent does not bind less than full-length RNA and double-stranded RNA impurities.

In an aspect, the RNA polymerase is covalently or noncovalently linked to template DNA and/or a nontemplate DNA as described above. In this aspect, the RNA polymerase can comprise an avidin-binding peptide, the nontemplate DNA comprises a 5'biotin label, and the RNA polymerase is noncovalently linked to the nontemplate DNA via a bead support that bind both the avidin-binding peptide and the biotin.

The method can be conducted under low salt conditions of 0 to 50 mM, or high salt conditions of 50 to 1000 mM.

In another aspect, contacting further includes a capture DNA as described above.

In another aspect, the inventors have recognized that promoter binding that leads to synthesis of the desired RNA competes with the product rebinding that generates longer impurities. It has been previously shown that some of the energy of promoter binding is used to drive coupled melting of the DNA near the start site. Targeted "nicking" of the DNA in the nontemplate strand can increase promoter binding (for example, by reducing the barrier to DNA melting). Removing the barrier to melting near the start site will increase promoter binding. Thus, a method of preparing an amplified functional template DNA is described herein.

Figure 5:
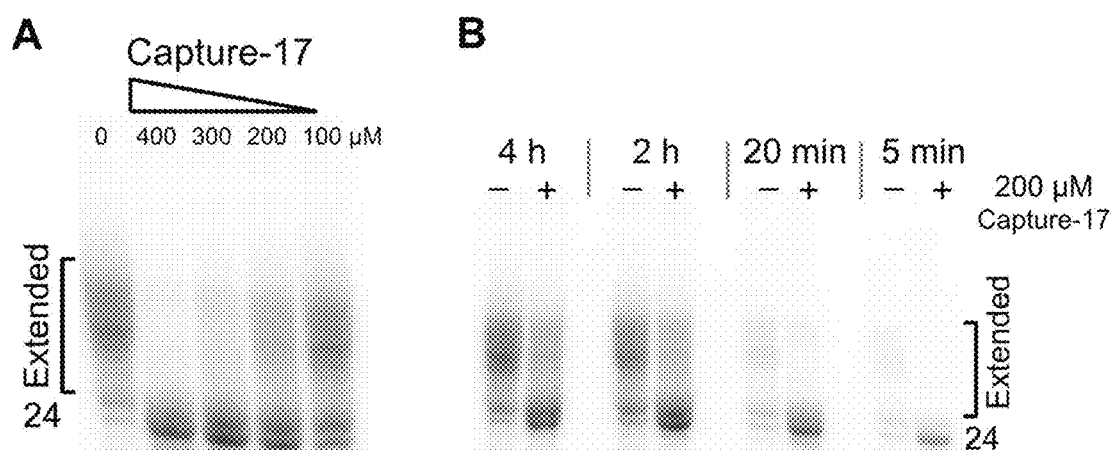
FIG. 5 shows the effect of concentration/stoichiometry of capture DNA. Denaturing (20% urea) gel electrophoreses analysis. All transcripts were labeled by [$\alpha$-$^{32}$P] ATP.
Figure 12:
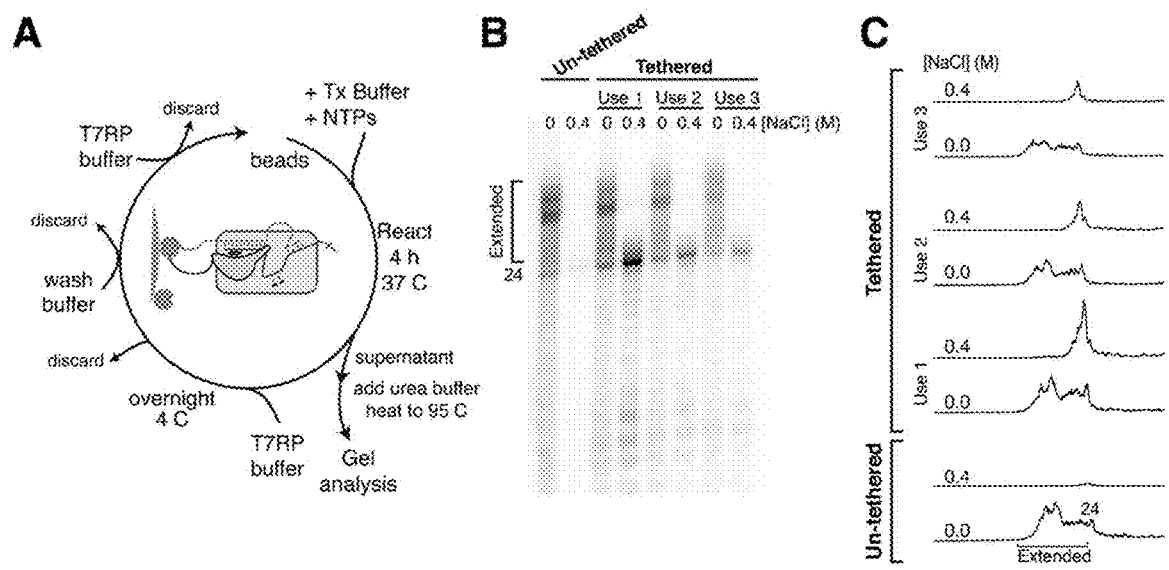
FIG. 12 shows the system can be reused.

A method of providing a modified, amplified functional template DNA comprises, providing a starting functional template DNA and an amplification primer, the amplification primer comprising one or more deoxyuridines on the nontemplate strand, under conditions for DNA amplification, amplifying the starting DNA functional template to provide an amplified DNA functional template, and excising the uracils from the amplification primer, providing the modified, amplified functional template DNA. Excising the uracils can be done using DNA glycosylase or mutants thereof. The modified, amplified functional template DNA has a weakened duplex in the melting region, which then strengthens promoter binding. The method optionally further comprises using exonuclease II to nick the modified, amplified functional template DNA. The resultant strengthening of binding will itself favor promoter binding over product re-binding, but then will also allow salt challenges. In direct analogy to the results of FIG. 5, the results presented in FIG. 12 demonstrate the predicted behavior: nicking the nontemplate DNA at position −4 significantly increases salt resistance, relative to the native control, and yields higher purity of the target RNA.

The foregoing approaches are expected to reduce the synthesis of impurities that are primer-extended RNAs longer than encoded by the DNA. However, impurities that are shorter than those encoded by the DNA can arise from an expected decrease in stability of the elongation complex as it approaches the end of a DNA functional template or by "bumping" of a leading polymerase by a trailing polymerase. What is needed are approaches that can reduce both types of impurities. In an aspect, a short DNA oligonucleotide complementary to the 3' end of the product RNA can be used to affinity purify product RNAs that are full length and not double-stranded at the end, thus reducing both contaminants.

In any of the methods disclosed herein, the functional template DNA can be a modified, amplified functional template DNA made by the method described above.

In an aspect, a method of purifying a product RNA, comprising
  adding a capture DNA to a reaction mixture for producing the product RNA, the reaction mixture comprising the product RNA, a functional template DNA for the product RNA, and an RNA polymerase under conditions for RNA synthesis; wherein the capture DNA is 10 nucleotides or longer in length, and wherein the capture DNA comprises a capture sequence complementary to a minimum of 10 nucleotides of the 3' terminus of the product RNA, and wherein the capture DNA is immobilized to a solid support;
  incubating the immobilized capture DNA and the reaction mixture to provide binding of the capture DNA and the product RNA,
  washing to remove unbound reaction components, and
  eluting the product RNA from the immobilized capture DNA.

In an aspect, eluting the product RNA is done at an elevated temperature of 40 to 95° C., although other means of elution such as a chemical denaturant (e.g., urea) or toehold-mediated strand displacement are possible.

In an aspect, the capture DNA is immobilized to the solid support via a linkage such as a PEG linkage. Exemplary solid supports include beads such as magnetic beads, as well as chromatographic supports.

Since capture of a product RNA with a capture DNA is stoichiometric, the overall purification yield of the foregoing purification is limited by the number of available capture DNA binding sites. In an aspect, the capture DNA comprises a plurality of capture sequences. Moreover, a porous bead material may be counter-indicated for capturing mRNA length RNAs, as the size of the pores may not accommodate the large polymeric RNA. A rolling circle amplification strategy to prepare a capture DNA comprising a plurality of capture sequences may be used to overcome these issues.

Figure 20:
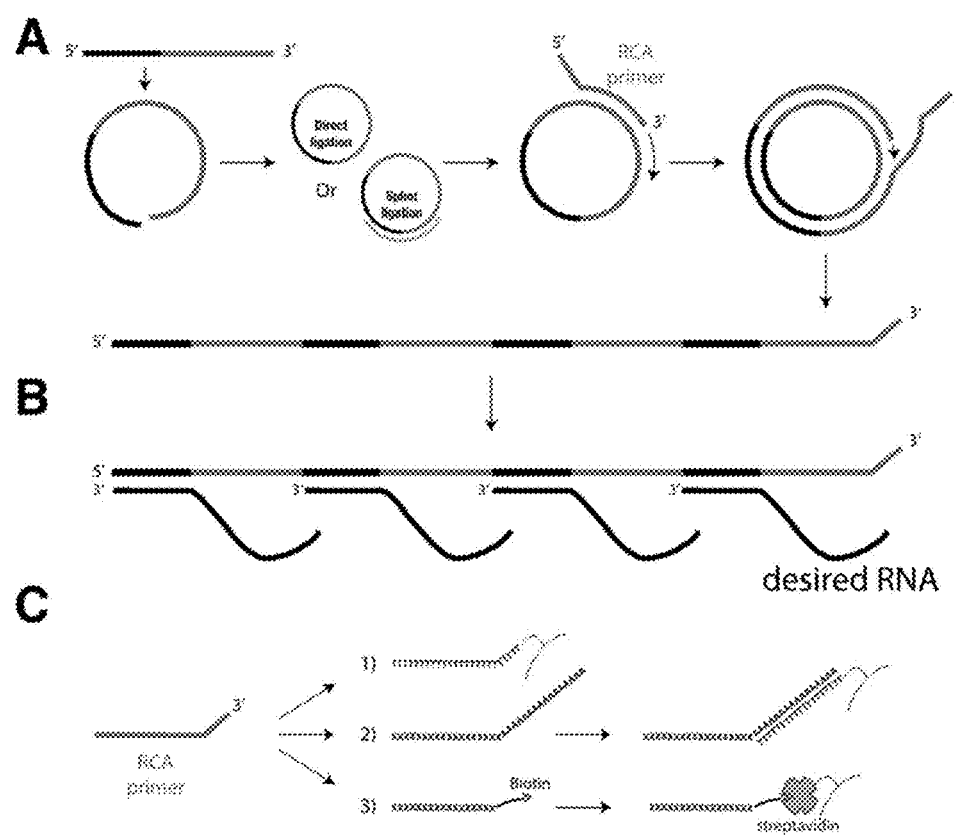
FIG. 20 shows rolling circle amplification of capture DNA.

Rolling circle amplification (RCA), shown in FIG. 20A, is used to generate capture DNA with repeating sequence elements. Thus, a single stranded capture DNA attached to a solid support might now harbor 10-100 binding elements to capture product RNA 3' ends, as illustrated in FIG. 20B. As shown in FIG. 20A, linear DNA containing the reverse complement (capture DNA) of the 3'product RNA sequence is ligated to form a circular DNA functional template. A primer is then extended using a strand displacing DNA polymerase to generate a long capture DNA containing repetitions of the capture sequence. As shown in FIG. 20B, the RCA construct can dramatically increase the capacity of any immobilization system. As shown in FIG. 20C, an RCA primer can attach to solid support for purification via a variety of means: 1) beads with covalently attached dT25 are commercially available and can anneal to a dA25 sequence engineered into the RCA template; 2) using the same beads, the primer could contain free dA25 to allow binding to the beads, and 3) an arbitrary priming sequence could be attached to an affinity tag such as biotin, for capture on complementary solid support.

There are a variety of approaches to preparing an RCA primer that is attached, or can be attached, to solid supports. Three are shown in FIG. 2C. In (1) dT25 covalently attached to non-porous magnetic beads is commercially available, and all or part of the dT25 element could anneal to dA25 engineered within the RCA template to prime extension. In (2) a dA25 element in the RCA primer, but external to the cyclic template would provide for noncovalent attachment to the same beads with covalently attached dT25. In (3) the RCA primer could contain a more traditional affinity tag, such as biotin for capture by streptavidin-coated beads. These are but three of a variety of immobilization approaches that would be viable in such a system.

The invention is further illustrated by the following non-limiting examples.

EXAMPLES

Example 1: RNA 3' End Sequestration

Materials and Methods

Reagents. DNA oligonucleotides used as transcription functional templates and as capture DNAs, and synthetic RNA for self-primed extension reactions, were purchased from Integrated DNA Technologies (IDT). All 'high yield' transcription reactions were conducted using HiScribe™ T7 High Yield RNA Synthesis Kit (New England BioLabs). For self-primed extension reactions, T7 RNA polymerase was prepared and purified in house.

RNA self-primed extension reactions. Reactions with synthetic RNA, in the absence of promoter DNA, were conducted with 25 µM synthetic RNA in the presence of 0.5 µM T7 RNA polymerase and 0.4 mM each of guanosine triphosphate (GTP), cytidine triphosphate (CTP), adenosine triphosphate (ATP), and uridine triphosphate (UTP). Reactions were carried out at 37° C. for both 5 min and 4 h in a transcription buffer containing 15 mM magnesium acetate, 30 mM 4-(2-hydroxyethyl)-1-piperazineethanesulfonic acid (HEPES), 25 mM potassium glutamate, 0.25 mM ethylenediaminetetraacetic acid and 0.05% Tween-20. For self-primed extension reactions in the presence of capture DNA, DNA oligonucleotides, complementary to the 3' end of RNA and containing 3' amino modification were added to reaction mixtures to a final concentration of 25 µM.

Transcription reactions. All reactions were performed using partially single-stranded DNA constructs, in which the nontemplate DNA oligonucleotide extends downstream only to position +2 (1, 41). All 'high yield' transcription reactions were carried out in the presence of 2 µM each of nontemplate and template DNA oligonucleotides, 7.5 mM of each NTP, and 1.5 µL T7 RNA polymerase Mix™ (New England BioLabs) in an overall 20 µL reaction volume at 37° C. for 4 h (unless noted otherwise). High yield transcription reactions in the presence of capture DNA additionally contained 400 µM (unless noted otherwise) capture DNA. RNase Inhibitor Murine (New England BioLabs) was added to a final concentration of 1 U/µL in all reaction mixtures. Both self-primed extension and transcription reactions were heat inactivated at 70° C. for 5 min.

Gel electrophoretic analyses. Reaction products were analyzed with 20% polyacrylamide, denaturing (7 M urea) gel electrophoresis. For self-primed extension reactions, the 5' end of the synthetic RNA was labeled by incubating 50 µM synthetic RNA with [γ-$^{32}$P] ATP (PerkinElmer) and 1 µL (10 Units) of T4 polynucleotide kinase (New England BioLabs) in a 10 µL reaction volume at 37° C. for 30 min. Labeling was inactivated by heating at 65° C. for 20 min. Transcribed RNAs were labeled by including [α-$^{32}$P] ATP (PerkinElmer) in the reaction mixture (without reducing the concentration of ATP). All gel experiments were repeated at least twice and showed no significant differences. Quantifications of gel data, using ImageJ v1.52a on unprocessed and uncompressed TIF output.

Results

Figure 2:
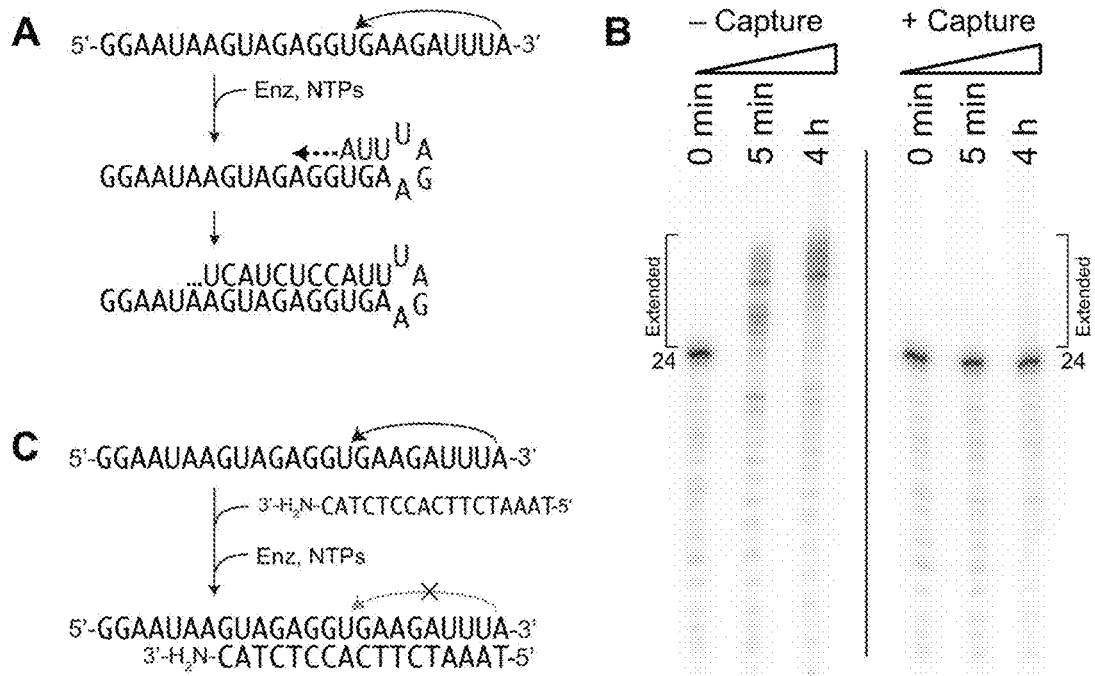
FIG. 2 shows inhibition of self-primed extension of synthetic RNA.

The determination that 3' end additions arise from (transient, active site bound) RNA structures in which the 3' end of the nascent RNA folds back on itself to prime extension, points to a potential intervention to competitively inhibit this process. The addition to the reaction of a short capture DNA complementary to the 3' end of the expected runoff RNA should drive formation of an RNA-DNA hybrid, as shown in FIG. 2, inhibiting self-primed extension. However, the possibility exists that RNA polymerase might in turn carry out primed synthesis from the 3' end of the capture DNA, generating partially chimeric double stranded impurities. To prevent such 3' extension of the DNA, for all capture DNAs used here we replaced the 3' sugar hydroxyl of the 3' terminal base with an amino group. While other 3' sugar modifications should similarly prevent nucleotide addition (phosphoryl transfer), 3' amino modification of DNA is commercially available during synthesis, at minimal added expense.

Self-primed extension of synthetic RNA is inhibited by 3' complementary capture DNA: Our previous work demonstrated self-primed extension of a specific 24-base RNA, synthesized as runoff from a DNA functional template or synthesized chemically. In that earlier work, we demonstrated very efficient self-primed extension from synthetic RNA, in the absence of T7 promoter DNA. The (same) synthetic RNA construct shown in FIG. 2A (25 µM) was incubated with T7 RNA polymerase and 0.4 mM of each NTP for 0 min, 5 min and 4 h at 37° C. The results shown in FIG. 2B in the absence (−) of 25 µM capture DNA show that in a 5 min reaction the synthetic RNA readily extends to longer RNA products that are chased to still longer products over 4 h, as observed previously.

As predicted, the results in FIG. 2B show that in the presence (+) of 25 µM of the 17-base capture DNA (FIG. 2C), self-primed extension is dramatically inhibited. This demonstrates that the presence of 3' complementary single stranded capture DNA is an effective way to competitively prevent 3' end additions.

Effect of varying the length of capture DNA in self-primed extension: The above data confirm that 17 bases of complementarity provides sufficient target affinity for maximal competitive binding. How short can capture DNA be to still effectively compete with functional binding of the free RNA to RNA polymerase? To test the effect of the length of capture DNA, we conducted self-primed extension reactions with 25 µM synthetic RNA in the presence of 25 µM capture DNA oligonucleotides with lengths of 14, 11 and 9 bases and compared them with 17-base capture DNA. All capture DNAs were designed to hybridize to the RNA from its 3' end, included a 3' amino modification, and were added to the reaction in equal concentrations to the synthetic RNA.

Figure 3:
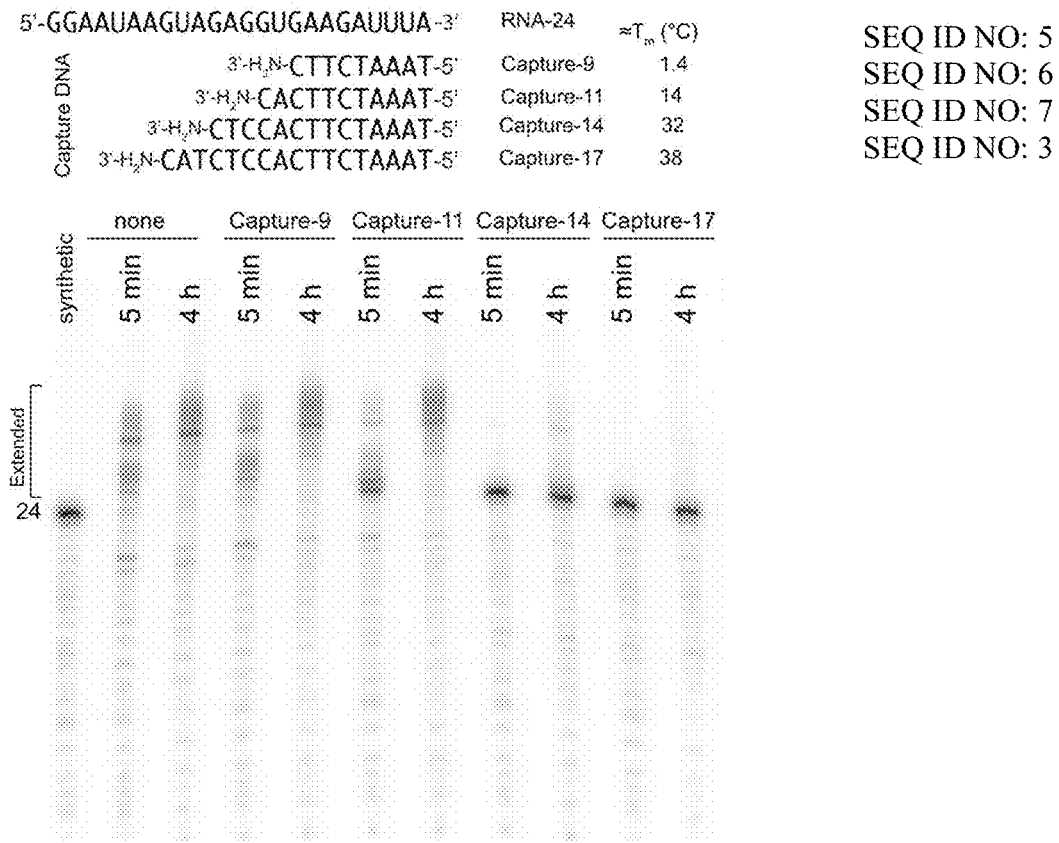
FIG. 3 shows the length optimization of capture DNA. Denaturing gel analysis, in the absence and presence of 3'-modified complementary capture DNA oligonucleotides of lengths 9, 11, 14 and 17-bases. Reactions were carried out at 37° C.; approximate predicted melting temperatures are shown for the RNA/DNA duplexes. The sequence of the RNA is presented for reference.

As shown in FIG. 3, a 9-base capture DNA (Capture-9) is unable to compete well with self-primed extension; the product profiles at both 5 min and 4 h are similar to those in the reaction containing no capture DNA. In contrast, the 11-base capture DNA (Capture-11) limits self-primed extension in a 5 min reaction but shows significant self-primed extension in a 4 h reaction. To a first approximation, at 37° C., the 14-base capture DNA (Capture-14) functions about as well as the 17-base capture DNA (Capture –17) in preventing unwanted self-primed extension.

Capture DNA prevents self-primed extension during high yield transcription: We have previously shown that, as commonly carried out, when pushing transcription reactions to high yield conditions (for example, 7.5 mM each NTP, and 4 h incubation at 37° C.), the desired runoff RNA can be a minority of the product. The high concentration of runoff RNA drives its rebinding to the polymerase to effectively compete with de novo initiation, and through the mechanism described above, generates n+1, n+2 and substantially longer RNA products. Just as a 3' complementary capture DNA can block rebinding; we expect that it should also inhibit rebinding from competing with initiation during transcription. To test this expectation, we added excess capture DNA to an in vitro transcription reaction with functional template DNA encoding the above 24-base RNA (with the same 3' end as above, and with only a slight difference in the sequence from position+4 to +6).

The results shown in the lanes labeled "24" in FIGS. 4A and 4B demonstrate that, as expected, the presence (+) of 400 µM 3' complementary capture DNA during a 4 h, high yield transcription reaction dramatically reduces formation of primer-extended products relative to the reaction in the absence of capture DNA (—). Encoded expected length RNA product increases substantially, while primer-extended products are reduced dramatically.

We previously observed that not all RNAs efficiently prime self-extension. To confirm that the presence of capture DNA does not interfere with synthesis of RNAs with low propensity to form primer extended products, we carried out identical transcription reactions on a functional template encoding RNA-24Alt that has been shown not to generate large amounts of longer RNA products. The results presented in FIG. 4 in the lanes labeled "24Alt" confirm similar transcription profiles in both the presence (+) and absence (−) of capture DNA complementary to 24Alt RNA, confirming that capture DNA has no negative effect on transcription efficiency.

Figure 4:
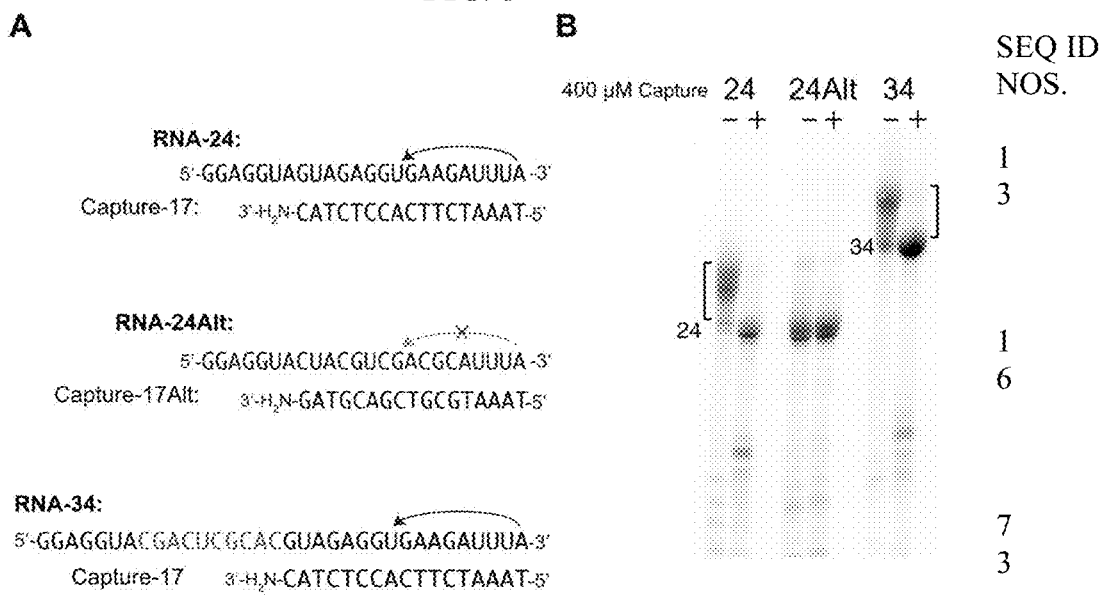
FIG. 4 shows capture DNA eliminates self-primed extension during RNA synthesis. Presence of 3'-complementary capture DNA sequesters product RNA, inhibiting self-primed extension during transcription.

Generalizability of the 3' capture DNA— length and sequence of the RNA: The RNAs synthesized above are short, allowing high resolution in the electrophoretic analysis of primer extended RNA products. The capture DNA at 17 bases, however, is only a bit shorter than the 24-base RNA itself. In order to extend the observation to longer length RNA, we used the same 17-base 3' complementary capture DNA to sequester a RNA with the same 3' terminal sequence, but with a 10 base insertion in the upstream, uncaptured region of the RNA, yielding a 34-base RNA, labeled "34" in FIG. 3. The results shown in FIG. 4 are essentially identical to the results on the shorter 24-base RNA, indicating the expected inhibition of self-primed extension in the presence of the complementary capture DNA.

Moreover, to confirm that this approach can be used as a general method to prevent self-primed extension we tested the effect of capture DNA for transcription on a functional template encoding a 24-base RNA with a different sequence, labeled "24B" in data not shown. The results show that addition of capture DNA to the transcription mixture can be used as a general method to inhibit self-primed extension for functional templates encoding different RNA sequences.

Titration of capture DNA oligonucleotide: The above experiments were carried out with 400 µM capture DNA in solution on the assumption that the RNA would not accumulate to levels higher than 400 µM. To examine the effect of the concentration (total amount) of capture DNA, we conducted transcription reactions under high yield condition in the presence of concentrations of capture DNA ranging from 400 µM down to 100 µM. The results presented in FIG. 5A, show that while 400 µM capture DNA dramatically reduces RNA 3' extension, reducing capture DNA concentration to 300 µM, 200 µM and 100 µM allows for increasing self-primed extension. These results are consistent with the expected stoichiometric titration of capture DNA by increasing product RNA. As product RNA concentrations exceed that of capture DNA, residual free RNA now rebinds to RNA polymerase and primes extension.

A more subtle interpretation might be that lower concentrations of capture DNA yield lower fractional formation of RNA-DNA capture complex, due to incomplete binding. To test this, we carried out transcription reactions in the presence of 200 µM capture DNA as a function of time. Consistent with the limiting stoichiometry model, at the lower reaction times of 5 and 20 min (and therefore lower RNA concentrations), this lower amount of capture DNA nevertheless effectively inhibits self-primed extension (FIG. 5B). The results confirm that the concentration of capture DNA (of tight binding length and sequence) needs only to exceed the final concentration of RNA synthesized in the reaction.

Discussion: Formation of longer RNA products during the synthesis of expected runoff RNA has been reported by various research groups over the years. The origin of these undesired longer RNA products synthesis has been attributed to different mechanisms, including turn-around synthesis, in which RNA polymerase switches to the nontemplate strand at the 5' end of the DNA template, nontemplated addition, and primer extension. In recent work using RNA-Seq to characterize products of transcription, we have shown that cis self-primed extension is the main mechanism leading to synthesis of these unexpected RNA products. In cis self-primed extension, as the runoff RNA accumulates, it can rebind to the RNA polymerase in a mode wherein it folds back on itself, priming transcription from its own upstream sequence as the template. Self-primed extension of the runoff RNA leads to a reduction in the yield of the expected RNA product, but more importantly, yields partially double stranded RNA impurities that may interfere with its applications (e.g., triggering the innate immune response in therapeutic applications).

In order to eliminate self-primed extension during high yield synthesis, we have introduced a new approach involving the addition to the reaction of a short capture DNA that is complementary to the 3' end of the expected runoff RNA. Hybrid duplex formation effectively sequesters the RNA 3' end, preventing it from looping back on itself (or binding in trans to another RNA) to prime RNA-templated extension. Furthermore, in order to exclude the possibility that RNA polymerase uses this capture DNA as a primer, we introduced a minor and inexpensive modification to capture DNA: replacement of the 3' hydroxyl group by an amino group in the current study, but other modifications should readily serve the same function.

Model studies with synthetic RNA. As reported previously, incubation of synthetic RNA, RNA polymerase, and substrate NTPs yields substantial self-primed extension. In contrast, the results presented in FIG. 2 show that the presence of a 1:1 ratio of 17-base capture DNA leads to a dramatic reduction in the formation of primer extended products.

Effective competition by 3' capture DNA should depend on the affinity of capture DNA for the 3' end of the RNA. Very approximate predictions suggest that 17-base capture DNA should bind to its target RNA with a (free in solution) T. of about 38° C. Shortening capture DNA to 14, 11, and 9 bases will weaken affinity, as reflected in the predicted melting temperatures. Not surprisingly, the results in FIG. 3 demonstrate that capture DNA complementary to only the 3' terminal 9 bases does not inhibit self-primed extension significantly. A 3' complementary 11-base capture DNA shows evidence of competition but is not effective at long reaction times. However, a 3' complementary 14-base capture DNA does provide effective competition. While it may seem surprising that oligonucleotides with relatively weak predicted (in solution) affinities compete well, it must be remembered that competition is relative to hairpins with only 2-3 base pair (internal) stems. Without being held to theory, we have proposed that the latter functions in self-primed extension due to interactions within the enzyme binding cleft that stabilize otherwise weak solution structures. It is possible that capture DNA benefits from similar stabilization, but of course, does not extend because of its 3' amino modification.

Application to transcription reactions. Extending the above to in vitro transcription reactions, we observed a similar inhibition of self-primed extension in the presence of capture DNA, without substantial inhibition of promoter-directed initiation (FIG. 4). While precise quantification of total RNA is complicated given the spread in product lengths, assays with a DNA template encoding RNA that does not undergo significant self-primed extension (24Alt in FIG. 4), does not show inhibition of promoter-directed synthesis by the appropriate 17-base capture DNA. This suggests that RNA-DNA hybrid binding to RNA polymerase is not overly strong, relative to promoter binding and de novo initiation.

To generalize these results to longer RNAs, we inserted 10 additional bases into the functional template DNA sequence encoding RNA-24, yielding a new construct encoding a 34-base RNA (RNA-34). The results shown in FIG. 4 yield identical behavior: in the absence of capture DNA, self-primed extension predominates, and in the presence, it is dramatically reduced. We fully expect that any length RNA will benefit from this approach.

As an aside, this experiment also provides preliminary information on the possible lengths of self-primed extension. In our original study, self-primed extension showed a range of extended lengths, but rarely continued to the maximum theoretical length, corresponding to the 5' end of the RNA. It could be that self-primed extension is fundamentally limited to short lengths, or alternatively, the functional complex may weaken as it nears the 5' end of the templating RNA. The results with promoter DNA encoding a 34-base transcript strongly suggest the latter. Noting the compression of longer length RNAs inherent in gel electrophoresis (see, for example, the DNA standards in FIG. 4), it appears that self-primed extension on 34-base RNA is extending to longer added lengths than on 24-base RNA. This predicts that still longer RNA-RNA duplex formation will occur on still longer RNAs, and indeed other studies have observed very long extensions.

To demonstrate the sequence generality of this approach, we tested the effect of capture DNA on functional templates encoding different RNA sequence with high abundance of self-primed extension products. Results not shown indicate inhibition of self-primed extension in the presence of capture DNA complementary to the 3' end of RNA.

It is expected in this competitive inhibition that when runoff RNA concentrations exceed that of capture DNA, the free residual RNA will now begin to prime self-templated extension. The results presented in FIG. 5A are consistent with this prediction, as lower concentrations of capture DNA during transcription allow for some self-primed extension during preparative-scale synthesis. Even 200 μM capture DNA allows for essentially complete inhibition of self-primed extension at short times/low RNA levels, but as transcription proceeds and RNA concentrations increase, self-primed extension begins to increase, as capture DNA is consumed.

Finally, most researchers will want to remove the capture DNA from the reaction and variety of approaches are common, as reviewed recently. The preferred solution will likely depend on the length of the RNA. While denaturing gel purification will readily separate product from capture DNA (and from enzyme, promoter DNA, and abortive products), for RNAs significantly longer than the capture DNA, simpler commercial kits exist.

Example 2: High Salt Synthesis

Figure 6:
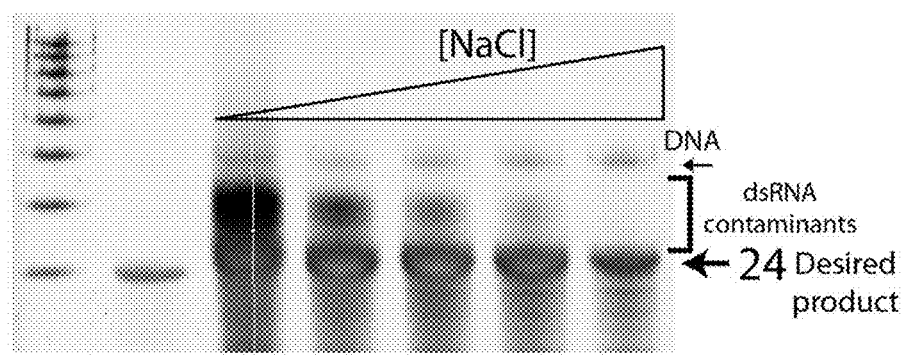
FIG. 6 shows increasing product purity with increasing salt in the reaction.

All protein-nucleic acid associations are sensitive to salt. Hence, in an approach that is independent, complementary and orthogonal to Example 1, increasing salt in the reaction can reduce/eliminate product RNA re-binding and extension as shown in FIG. 6. However, initial promoter binding, required for correct synthesis, also decreases significantly with salt. To restore binding, the functional template DNA was linked to the enzyme to ensure promoter binding, even in the presence of high salt (and to favor promoter-initiated transcription over other reactions, at all salt concentrations).

Figure 7:
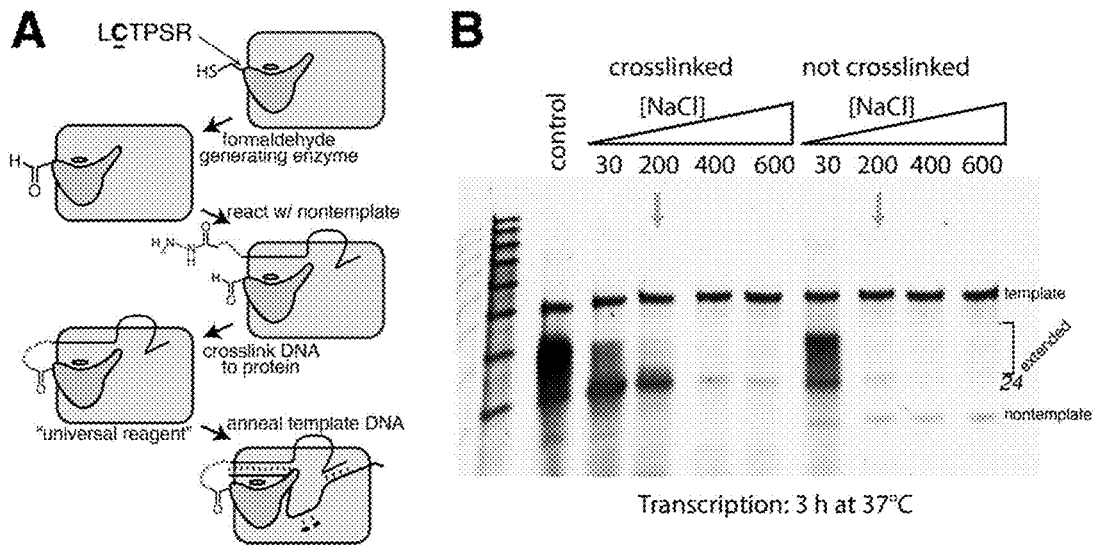
FIG. 7 illustrates an embodiment of tethered, high salt transcription.

To achieve salt-resistant promoter-directed transcription, RNA polymerase was engineered to contain a recognition sequence for the formyl glycine generating enzyme, introducing a unique aldehyde near the upstream end of the promoter DNA (guided by crystal structures). Synthesis of nontemplate DNA containing a 5' hydrazine, allows covalent coupling of the hydrazine to the aldehyde. This generates a "universal reagent" containing the nontemplate DNA tethered to the protein. A user can then add to the reagent template DNA containing DNA of fixed sequence upstream (to the left) of the transcription start site (indicated by an arrow in FIG. 7), with the desired RNA sequence encoded immediately downstream.

Transcription with this promoter-coupled enzyme now shows resistance to salt, allowing the desired, salt-dependent reduction in off-pathway reactions, while retaining promoter-directed transcription. As shown at 200 mM NaCl in FIG. 7, the result is dramatically more pure RNA relative to the untethered control. The "not crosslinked" controls demonstrate that without crosslinking, transcription is inhibited at 200 mM NaCl (or other salt).

In the above reaction, 100% coupling of the aldehyde-containing nontemplate DNA to the aldehyde containing protein has not been achieved. Higher overall yields can be achieved as the percentage of coupling is improved.

Example 3: High Salt In Vitro Transcription Using Promoter DNA and T7 RNA Polymerase Co-Tethered to Beads The goal of this study is to eliminate RNA product rebinding and extension, while retaining promoter-directed transcription. Both initial binding of T7 RNA polymerase to its promoter and rebinding of product RNA are stabilized by electrostatic interactions between the positively charged residues on the RNA polymerase surface and the negatively charged phosphate backbone of the DNA or RNA. As a result, increasing salt concentrations should destabilize both promoter binding and product rebinding. We have previously shown that covalently crosslinking an engineered cysteine (A94C) in the N-terminal domain of T7 RNA polymerase to a 3' thiol-modified template DNA creates a locally high concentration of the promoter near its binding site, allowing promoter binding, even at high salt. Initiation proceeds well and at least some of these complexes transition to a stable elongation complex. Elongation complexes of T7 RNA polymerase are stabilized by a topological locking of the RNA around the template DNA in the enzyme active site and so are resistant to added salt concentrations up to at least 0.2 M NaCl.

In order to tether the polymerase to the promoter DNA and still allow functional initiation and substantial transition to elongation, we bound them each to Step-Tactin®XT magnetic beads. The N-terminal domain of T7 RNA polymerase (together with a hairpin loop from the C-terminal domain) forms the promoter binding platform and many N-terminal fusions of T7 RNA polymerase function well in promoter-directed transcription. Thus, we fused the Strep-tag® II peptide (WSHPQFEK; SEQ ID NO: 8) followed by a short and flexible peptide linker (GGS), to the N-terminus of recombinant T7 RNA polymerase. The Strep-tag® II peptide has nanomolar binding affinity to the specifically engineered Strep-Tactin®XT magnetic beads. We also prepared 5'—biotinylated nontemplate DNA (extending upstream from position –25 to position+2 downstream). Biotin is reported to have picomolar binding affinity to Strep-Tactin®XT magnetic beads. SEQ ID NOs. 9-14 were used in the following experiments.

To confirm that the Strep-tag®-II peptide addition at the N-terminus of T7 RNA polymerase does not affect transcription activity, we performed in vitro transcription reactions using Strep-tagged polymerase and promoter DNA encoding a 24mer RNA (RNA 24) under high yield solution conditions. A gel analysis (data not shown) demonstrates identical transcription profiles using T7 RNA polymerase and its Strep-tagged variant. This confirms that the addition of the Strep-tag®-II peptide has no adverse effect on the activity of T7 RNA polymerase. Similarly, biotinylating the upstream end of the promoter has no effect on promoter function (data not shown). Finally, we tested these constructs for transcription activity at 0.4 M added NaCl, and as expected for the uncoupled species, observed complete inhibition of transcription in all constructs.

Figure 8:
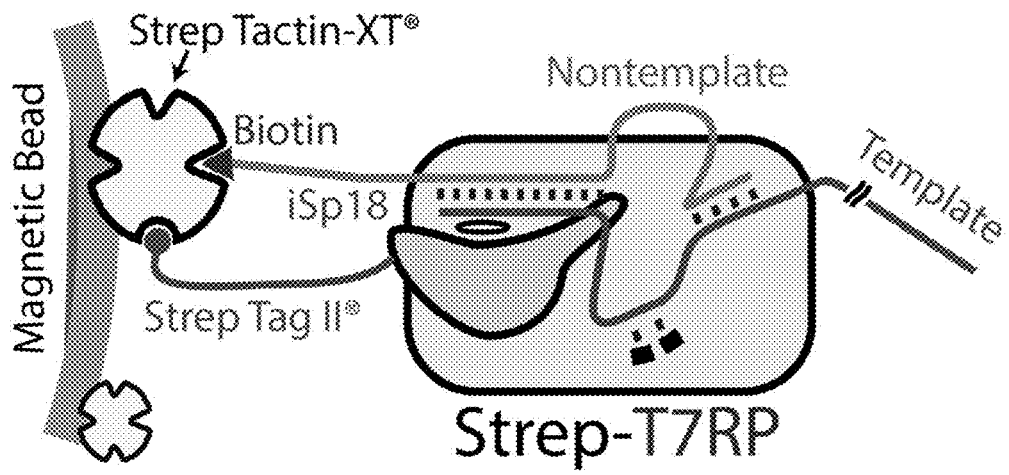
FIG. 8 illustrates a crosslinked transcription complex. T7 RNA polymerase containing an N-terminal Strep-tag®-II peptide and functional template DNA labeled with biotin at the 5' end of the nontemplate strand are bound to (tetravalent) StrepTactin®XT magnetic beads.

Tethered system favors promoter transcription at high salt: Having demonstrated that the DNA and protein modifications do not perturb promoter binding and transcription, we proceeded to test the tethered system for function. Given that at low salt the dissociation constant for duplex promoter binding by T7 RNA polymerase is ≈10 nM, we first pre-incubated the 5'-biotinylated nontemplate strand, template strand encoding a 24 base RNA and Strep-tagged T7 RNA polymerase at final equimolar concentrations of 0.8 µM. We then incubated the assembled promoter complex with beads coated with tetrameric Strep-Tactin® XT to form the tethered in vitro transcription system illustrated in FIG. 8.

We hypothesized that elevated salt concentrations weaken both on and off-pathway binding interactions, while tethering T7 RNA polymerase to the promoter should restore promoter binding by increasing the local concentration of promoter DNA compared to the free RNA in solution. To test the hypothesis with our tethered in vitro transcription system, we performed a comparative analysis of transcription between tethered and un-tethered systems as a function of increasing concentrations of NaCl. In order to see the direct effect on cis primed extension activity, we selected a functional template that encodes a 24mer RNA known to serve effectively in 3' primer extension. The gel analysis presented in FIG. 9A shows that as added NaCl concentration is increased from 0 M to 0.4 M in 0.1 M intervals, all transcription activity decreases for the un-tethered system, and is negligible at 0.4 M NaCl. In the tethered system, promoter binding is resistant to increasing salt and transcription proceeds, while product RNA rebinding to polymerase is inhibited, reducing the formation of longer products. By 0.3-0.4 M NaCl, primer extended products are dramatically reduced. At 0.4 M NaCl, the overall yield starts decreasing but the purity of the encoded RNA is at its highest. Overall, high salt transcription in the tethered system shows much higher purity with increased yield of the correct length product Synthesis of encoded RNAs is not impaired by tethering: Not all encoded RNAs participate in 3' self-extension. To confirm that tethered transcription does not have an effect on the fundamental efficiency of promoter driven transcription, we repeated the above comparative analysis with a functional template encoding a 24mer RNA (RNA-24Alt) that is known not to participate substantially in 3' primer extension reactions. The gel analysis presented in FIG. 10A shows the overall loss of yield in RNA transcription with increasing NaCl concentration, using un-tethered Strep-T7 RNA polymerase in solution. At 0.4 M NaCl (Lane 5), un-tethered transcription is mostly eliminated. FIG. 10A further shows that for the tethered system promoter driven on-pathway transcription is essentially unaffected by increasing salt concentrations up to about 300 mM added NaCl. The tethered enzyme is as efficient at producing encoded RNA-24Alt at 0.3M as it is at 0 M, as expected. In summary, the promoter driven transcription yields are not affected by high salt concentrations in the tethered in vitro transcription system. Users can define whether they would like to use 0.3 M or 0.4 M salt depending on their desire for yield versus purity.

Generality of the system: The results presented in FIGS. 9 and 10 use DNAs encoding 24 base RNAs. To test the generality of this system, we took the 24mer RNA introduced in FIG. 9 and inserted 10 bases at position+8 (data not shown). Paralleling the experiment of FIG. 9, we compare in FIG. 11 un-tethered and tethered transcription of RNA-34 at low (0 M) and high salt (0.4 M) concentrations. As predicted by the general model, the tethered in vitro transcription system produces only the encoded 34mer RNA at high salt. This result confirms that the system can be used for RNA of longer length to transcribe high yields of encoded RNA while preventing the formation of self-extended longer RNA impurities.

Biotinylated DNA and Strep-T7 RNA polymerase bind at adjacent sites on the tetrameric Strep-Tactin®magnetic beads: To encourage both enzyme and DNA to attach to the same tetramer in the above experiments, we preincubated (at low salt) tagged polymerase and labeled promoter DNA before adding the Strep-Tactin® XT magnetic beads. Following assembly, a high salt wash was used to remove components not strongly bound to the beads. As controls, we prepared tethered transcription complexes using DNA and T7 RNA polymerase with only one or neither of the two modifications. The resulting in vitro transcription reactions with DNA encoding RNA-24 under high yield conditions (data not shown) confirm that the absence of one or both of the modifications destroys RNA synthesis, both at low and high salt concentrations.

Despite the high affinity of T7 RNA polymerase for its promoter, we expected that some free enzyme or DNA would bind to the beads independently. Without a partner, these should be inactive in transcription. To test for enzyme immobilized without a promoter partner, we challenged an assembled and washed system encoding RNA-24Alt by introducing in solution unmodified promoter DNA encoding RNA-34Alt. At low salt, RNA polymerase without a partner will bind the free DNA encoding 34mer and transcribe it. Data not shown demonstrates this hypothesis to be correct. While at low salt, both 24Alt and 34Alt are transcribed at levels similar to that of untethered transcription, at high salt, only tethered RNA-24Alt is transcribed.

The system is stable and reusable: In this system, Strep-T7 RNA polymerase and functional template DNA are immobilized on Strep-Tactin® XT magnetic beads. This suggests that this bead-immobilized transcription complex could be re-utilized for multiple rounds of transcription. To test this, we carried out one round of transcription as above and stopped the reaction by the addition of EDTA to 50 mM. As illustrated in FIG. 12A, the beads containing immobilized transcription complex were then separated from the supernatant (containing RNAs, NTPs, and transcription byproducts) using a magnetic stand. After resuspension in [wash/transcription] buffer, they were stored overnight at 4° C. The following day, the beads were washed again in wash buffer and then resuspended in transcription buffer containing fresh NTPs to initiate a second round of transcription. This cycle was repeated a third time. The results from all three rounds of transcription are compared in FIGS. 12B and 12C. Although there is some loss in activity with each cycle, the system is reasonably robust.

The gel analysis presented in FIG. 12B compares the products at each reaction cycle, under both low (0 M) and high (0.4 M) added salt conditions. The results show that the system can be used at least three times, with only a small loss in yield, by simply washing the immobilized complex and introducing transcription buffer with fresh NTPs.

Discussion: Transcription in vitro by T7 RNA polymerase is widely used to synthesize RNA of diverse lengths and sequences, due to the promoter specificity and robust nature of this system. It is, however, known that under high yield synthesis conditions, this enzyme can generate extensive non-promoter specific activity that contaminates the product pool with other than encoded RNA products. The RNA field has long followed a two-step methodology in order achieve high yields of desired RNA: 1) high yield transcription using T7 RNA polymerase followed by 2) (sometimes extensive) purification of the encoded RNA using gel or chromatic purification methods. We have recently shown that the quest for high yield only exacerbates the production of undesired, longer products. As high concentrations of encoded RNA accumulate, T7 RNA polymerase rebinds the product RNA and extends it via primed extension, independent of the promoter. This leads to two problems: 1) heterogeneous longer than desired, (partially) double stranded RNA is produced and 2) since correct product RNA is extended to longer impurities, the net yield of the desired product decreases. In some cases, gel electrophoretic or chromatographic purification methods can address the first problem, but with further decreases in yield of the desired product. Purification approaches work best for relatively short RNAs, where the resolution of the purification is sufficient. Preparative separation of a target 300 base RNA from products extended by 20-30 bases, for example, is often beyond most approaches. With increased emphasis on mRNAs many kilobases in length, other solutions are required.

In an attempt to decrease non-promoter driven activities during transcription, we introduce a novel and exclusively promoter specific in vitro transcription method using bead tethered promoter DNA and T7 RNA polymerase under high salt conditions. The latter inhibits all polymerase-nucleic acid interactions. To restore only promoter specific transcription, we tether Strep-tagged T7 RNA polymerase and biotinylated promoter DNA to Strep-Tactin® XT beads, bringing the enzyme in close proximity to its promoter to drive promoter binding, even at high ionic strength.

Figure 9:
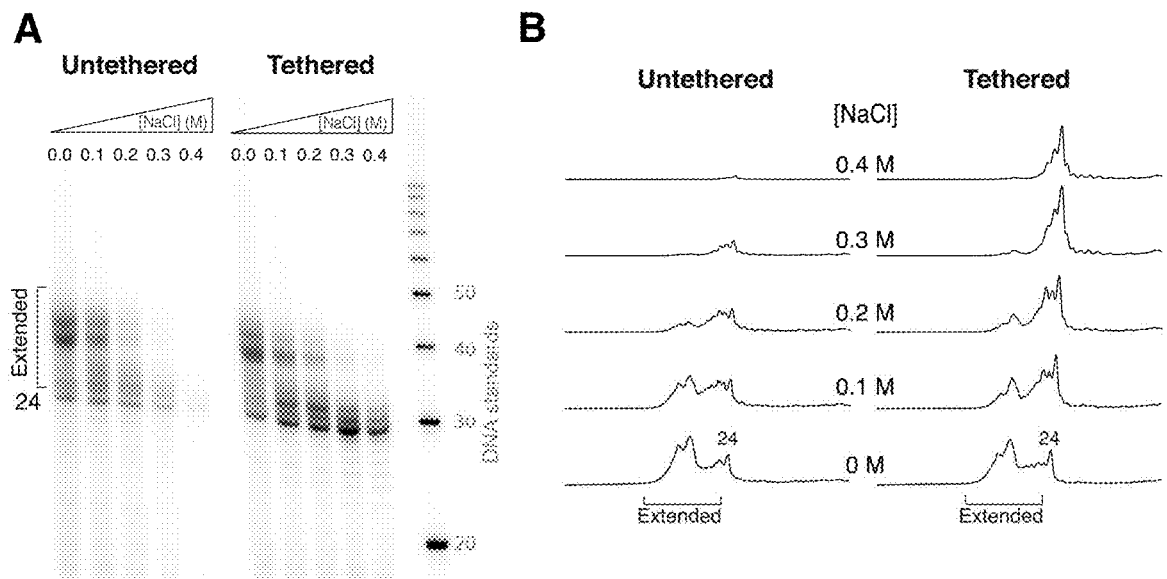
FIG. 9 shows tethered, high salt transcription dramatically reduces primer extension.
Figure 10:
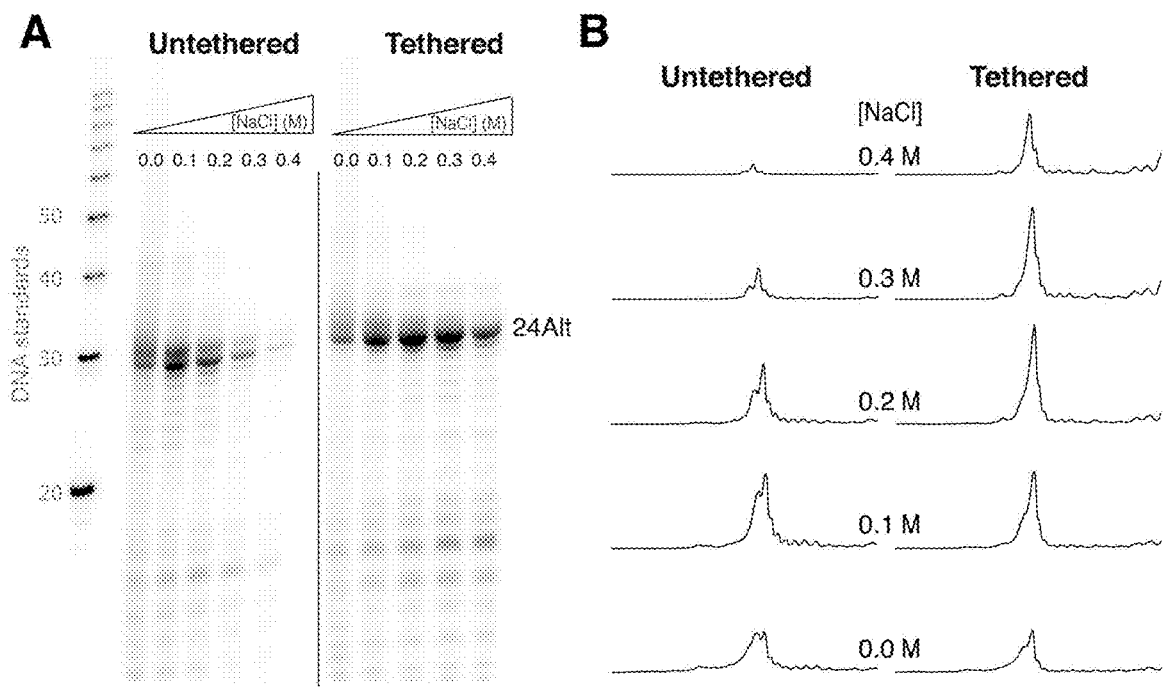
FIG. 10 shows tethered, high salt transcription does not impair transcription.

While increasing the salt concentration leads to complete inhibition of all enzymatic activity in the untethered system, as shown in FIGS. 9 and 11, in the tethered system high salt inhibits the undesired cis-primed extension activity of T7 RNA polymerase, while allowing promoter-directed transcription. As expected, the production of primer extended products decreases, leaving higher amounts of the encoded length, unextended product. At sufficiently high concentrations of salt, even tethered transcription begins to decrease, again as expected. For these constructs, a practical optimum of about 0.3 M added NaCl provides a good trade off of purity vs yield. While these experiments have been carried out on relatively short RNAs, the almost identical behavior of 24 and 34 length encoded transcripts (FIGS. 9 and 11, respectively) argues that this result should be generalizable to any length RNA (e.g., mRNA and lncRNA), as the model would predict.

In an attempt to characterize the salt dependence of promoter-driven transcription with less dependence on primer extension, we used a sequence, 24Alt, previously observed to yield less of the resolvable primer extended products. The result in FIG. 10 that 0.1 M added NaCl leads to increased 24mer suggests that this construct (untethered) is, in fact, driving primer extension, but as observed in the gel, in a more dispersed heterogeneous way. Indeed, there is a detectable "smear" across lengths longer than 24 bases, which for the untethered system decreases concomitant with an increase in 24mer product at 0.1 M added NaCl. For the tethered system, this trend continues to at least 0.2 M added NaCl. Thus, primer extension, under these conditions, appears to be more sensitive to salt than promoter-directed transcription.

Examples 1 and 2 are orthogonal and so the approaches could be combined for added benefit. One could use tethered, high salt transcription in the presence of 3' capture DNA, since a wealth of prior studies shows that binding of capture DNA to RNA should show very minor dependence on salt at these levels.

Local "tethering" of the promoter near its binding site, promoter binding (and transcription) persists, even at high salt. Thus, the re-binding that leads to dsRNA can be reduced, while maintaining correct transcription.

Crosslinking has been done by two completely different means, demonstrating that it is not the nature of the crosslinking, but the crosslinking itself that is achieving the outcome.

In one case, elevated salt was not needed. Without being held to theory it is believed that the crosslinking allows promoter binding to compete well against product rebinding, even at normal, low salt conditions. Fine tuning the linkage will enhance this effect.

Example 4: Flow Chamber

Figure 13:
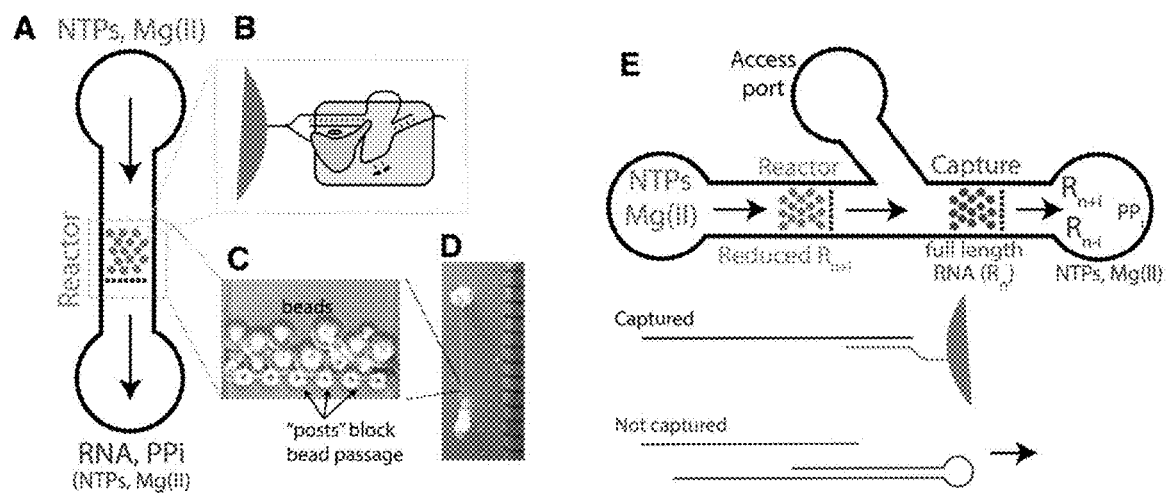
FIG. 13 illustrates flow reactors for synthesis.

A flow chamber is being developed wherein polymerase and DNA are tethered to each other, but also to a solid support (beads), as in Example 3 and FIG. 13. In a flow system, product RNA is continuously removed from the reactor and so the product cannot be reused to form dsRNA. Without being held to theory it is believed that this approach will reduce unwanted side reactions. In addition, all by-products of the reaction, including pyrophosphate and abortive RNA transcripts are continuously removed from the reactor as new substrate NTPs are added. In conventional high yield transcription, both depletion of substrate and accumulation of byproducts such as pyrophosphate ultimately lead to cessation of transcription. A flow reactor could synthesize RNA, unattended, at a uniform rate for very long lengths of time.

This approach is orthogonal to Examples 1 and 2. Thus, if desired, a flow reactor could be run at elevated salt concentrations.

In a next generation device, shown in FIG. 13E, a downstream chamber containing immobilized beads could serve as an affinity capture mechanism to "fish" out only full length, single stranded RNA from the reactor effluent. RNA less than full length (lacking the 3' target sequence) and RNA double stranded at its 3' end will flow through. If 3' capture DNA is included as input, it would contain an affinity tag orthogonal to tags used for tethering in the reactor beads.

The above reactors are "preparative" and could be scaled in size, as needed. High bead binding capacity argues that preparative reactions, which might normally be carried out in 0.5 mL reactions, could be carried out in 50 μL, or smaller, reactor chambers. Flow rates could be optimized to efficiently use substrate NTPs and, as noted above, the only limit to the run times would be capacity of the capture chamber (and the life of the enzyme; T7 RNA polymerase is very stable, generally). Such devices are very inexpensive to manufacture and could be readily mass produced (and parallel reactors would be simple to implement on a single chip). Pump systems designed to drive flow under computer control are readily available at relatively low cost. The flow chips may be disposable. As noted in Example 2, bead-coupled "universal reagents" could be produced (and stored) in bulk, and then partnered at run time with user-provided template strand DNA encoding the desired runoff RNA. Alternatively, double stranded DNA containing the appropriate 5' modification could be prepared by PCR, using a universal modified primer.

Figure 14:
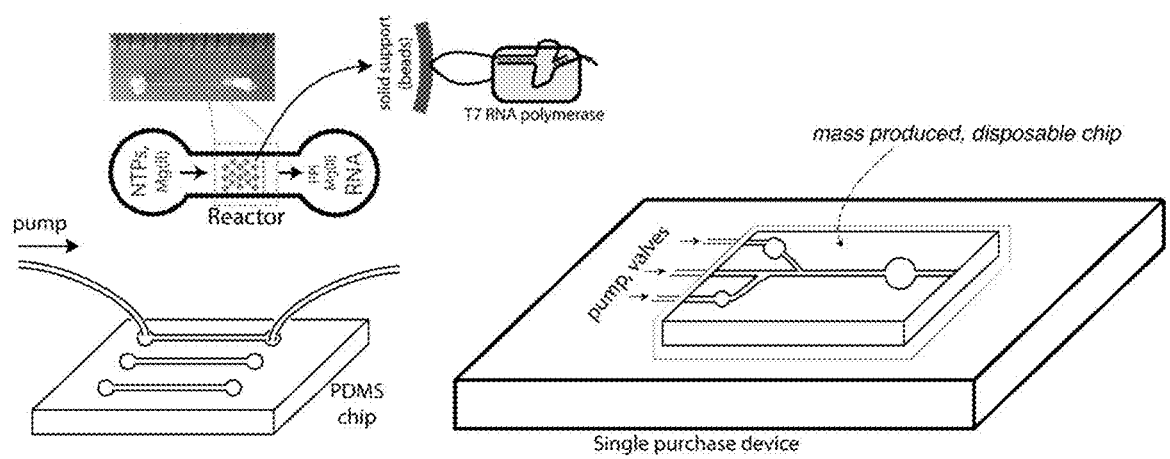
FIG. 14 shows an initial prototype flow chamber (left) alongside an example production device (right).
Figure 15:
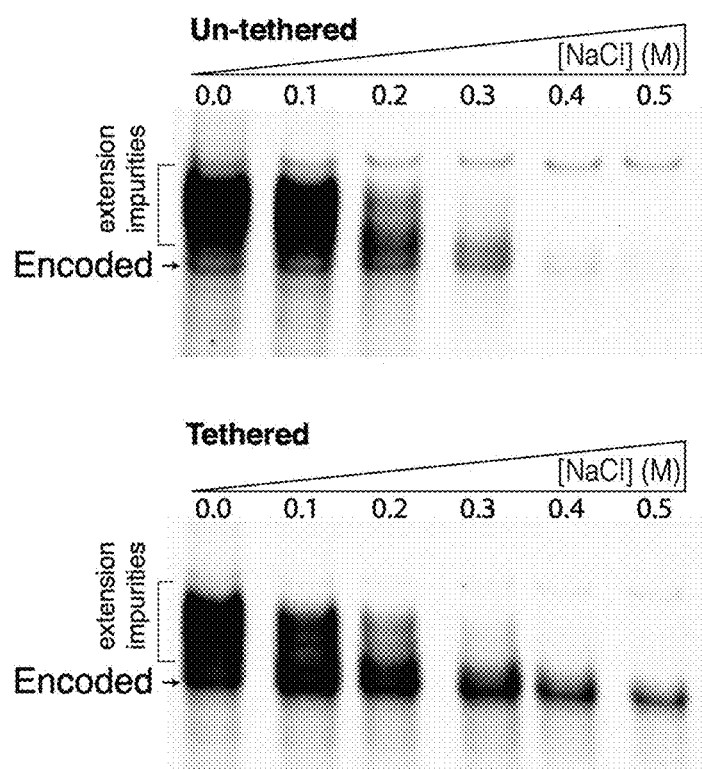
FIG. 15 shows the dramatic improvement in batch synthesis using enzyme and DNA tethered to a solid surface, modeling synthesis in a flow reactor.

FIG. 14 shows an initial prototype flow chamber alongside an example production device. FIG. 15 shows the dramatic improvement in batch synthesis using enzyme and DNA tethered to a solid surface, modeling synthesis in a flow reactor.

Example 5. Alternate Tethering Schemes

FIG. 16 illustrates alternate tethering schemes. FIG. 17 shows A) Covalent attachment of the nontemplate DNA to a Halo-Tag domain fused to the polymerase generates a "universal reagent." Users provide template DNA encoding RNA of interest. B) For long (e.g., mRNA) RNA, a Br-modified DNA duplex can be generated (via PCR), and then (covalently) bound to Halo-T7RP as above.

Example 6: Strengthening Promoter Binding to Disfavor Off-Pathway Reactions

Figure 18:
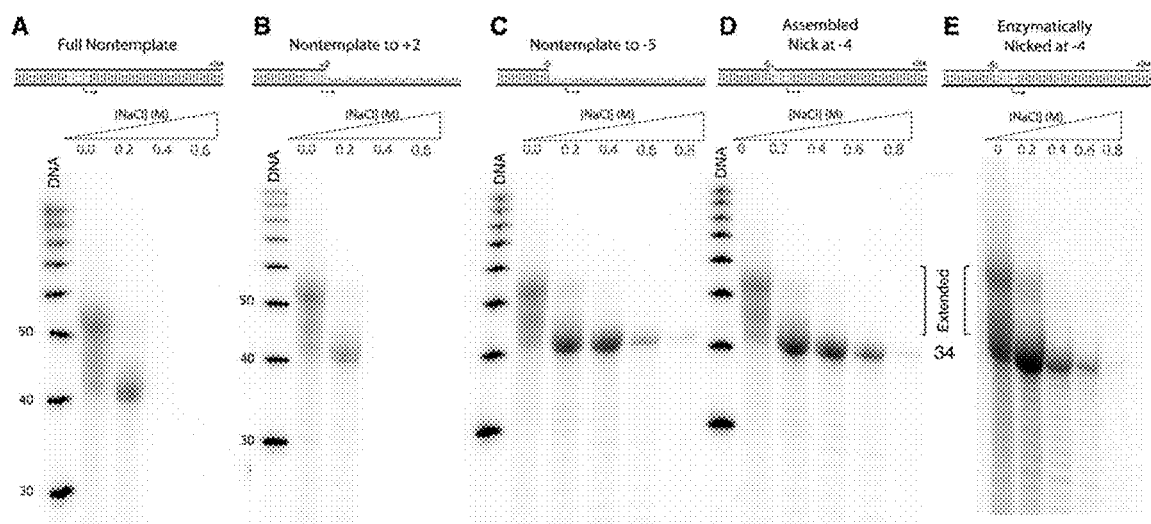
FIG. 18 shows that nicking the nontemplate DNA at position −4 yields a response representative of the expected stronger promoter binding: the salt resistance, relative to the native control, is increased and the reaction yields higher purity of the target RNA. Nontemplate to +2 (B) mimics full nontemplate (A) and shows significant salt sensitivity. Nontemplate to −5 (C) removes the barrier to melting, strengthening binding, which leads to salt resistance. Introduction of a nick at −4 by assembling three pieces of DNA (D) reduces the barrier to melting and confers salt resistance. A nick can also be introduced enzymatically (E) and confers the same resistance. The last example is important for applications using arbitrary length, PCR-generated DNA functional templates, as deoxyU can be introduced in the 5' PCR primer.
Figure 19:
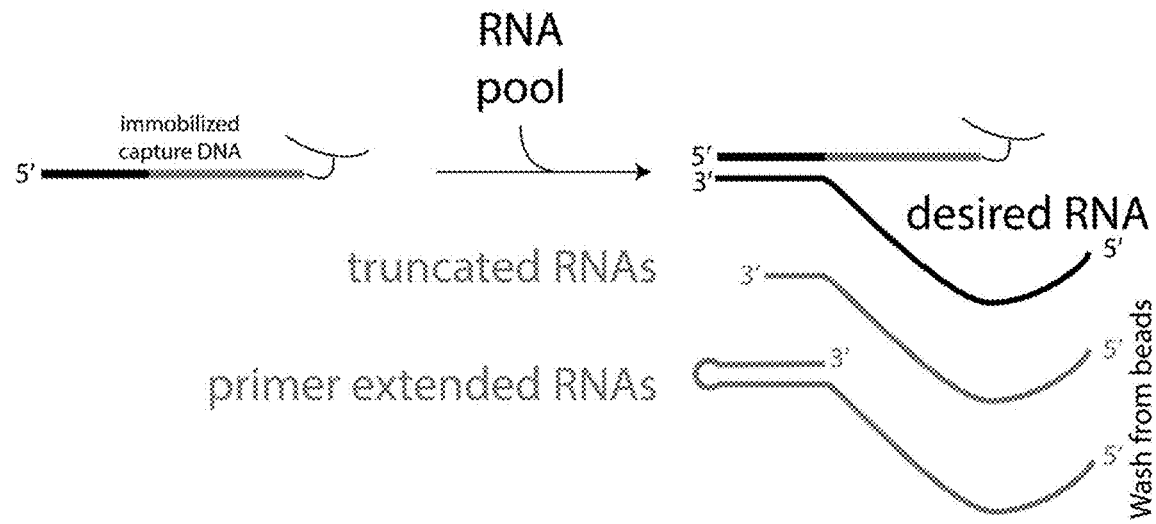
FIG. 19 illustrates an affinity capture method for product RNAs. DNA with a component complementary to the 3' end of the desired RNA selectively binds only RNAs with a free 3' end, allowing for affinity chromatography or other affinity separation to purify only full length, single-stranded target RNA.

FIG. 18 shows that nicking the nontemplate DNA between positions −5 and −4 yields a response representative of the expected stronger promoter binding: the salt resistance, relative to the native control, is increased and the reaction yields higher purity of the target RNA. FIG. 18B shows that rather than assembling DNA from single stranded fragments, PCR generated, double-stranded DNA can be nicked between positions −5 and −4 after PCR. Incorporation of dU at equivalent position −4 in the PCR primer used to generate the double-stranded DNA provides a unique recognition signal for Thermolabile USER (Uracil-Specific Excision Reagent) II Enzyme, Example 7: Capture of Product RNA An initial prototype for the capture of product RNA with a nontarget DNA, is shown in FIG. 19, where affinity purification targets (only) RNA containing the terminal, encoded sequence, in single stranded form. As shown in FIG. 19, nontarget DNA immobilized on a solid support contains a 5' terminal sequences that is complementary to just enough of the 3' end of the full-length product RNA to provide binding at low or room temperature. The support is then washed to remove truncated RNAs with a shortened capture sequence and ds RNAs, whose capture sequence is hidden within RNA structure. Finally, the full-length RNA can be released by elevated temperature.

In FIG. 19, the red region of the immobilized capture DNA is designed to match the 3' terminal sequence of the RNA. The length of this capture sequence is designed to have a moderate melting temperature. Binding would occur below that temperature; release would occur above that temperature.

Figure 21:
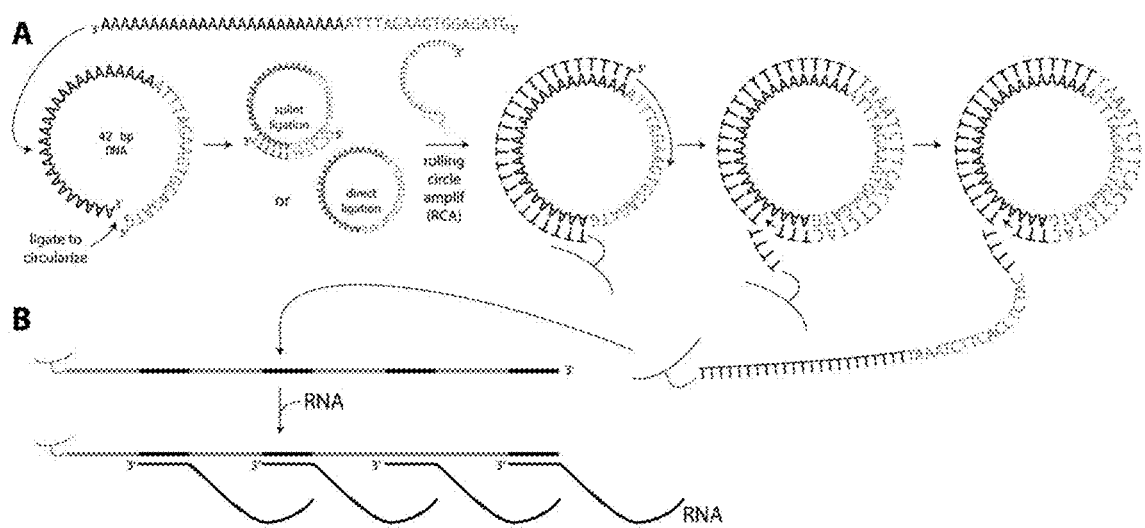
FIG. 21 illustrates an example of rolling circle amplification.

The region in blue could be an arbitrary linking sequence of DNA or might be a "tethering" linkage, such as polyethylene glycol. The intent is to provide some distance between the solid support and the capture sequence Example 8: RCA Amplification of Capture Sequence FIG. 21 illustrates an example of rolling circle amplification. FIG. 21A) capture DNA containing a sequence identical to the 3' end of the desired RNA followed by dA25 is obtained commercially. The capture DNA is then circularized with ligase (either with or without a "splint" DNA to aid circularization). dT25 DNA is covalently attached to beads is then used to prime rolling circle amplification. The product is capture DNA covalently attached to magnetic beads that contains many target sites for purification. The above illustration shows 4 sites, but a much larger number is possible per DNA. In data not shown, lengths that are long enough to increase the viscosity of the solution noticeably have been achieved. For this example, a DNA 1,000 bases in length would contain about 24-25 binding sites for RNA. FIG. 21B) the resulting bead-capture DNA conjugate is then used as in the method of FIG. 19 to purify only correct length RNA.

While this example uses commercially available dT25 covalently attached to beads, but any sequence and any attachment approach should work equally well.

The design of the capture sequence can be such that RNAs truncated by as few as 1-3 nucleotides might be discriminated. Washes at increasing temperatures could allow for the discrimination of weakly from strongly bound RNAs.

An alternative purification approach, magnetic beads could be replaced with a conventional chromatographic support. The target sequence would then be designed to allow weaker (but still significant) binding to the target RNA. Purified RNA would then be separated via a more conventional approach, such as collecting fractions as they pass through the column. RNAs containing the target sequence for capture would move most slowly through the column and would elute last. Discrimination of fractions collected might allow distinguishing RNAs shortened by as few as 1 base (which might bind to the target DNA, but more weakly and so be retarded less in its migration). This latter approach might allow for even larger scale up, should that be desired.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of synthesizing a product RNA, the method comprising
preparing a reaction mixture comprising a functional template DNA for the product RNA, and an RNA polymerase under conditions for RNA synthesis, wherein the functional template DNA and the RNA polymerase are immobilized to a solid support, and wherein the reaction mixture and the solid support are contained in a reaction chamber of a fluidic chip, the fluidic chip comprising fluidic paths for reagent delivery and product RNA removal, and
synthesizing the product RNA in the reaction mixture and continuously removing the product RNA from the reaction chamber while flowing fresh RNA synthesis reagents into the reaction chamber,
wherein the RNA polymerase comprises an avidin-binding peptide, the functional template DNA comprises a 3' or 5' biotin label respectively, and the RNA polymerase is noncovalently linked to the functional template DNA via a bead support that binds both the avidin-binding peptide and the biotin.

2. The method of claim 1, wherein the reaction chamber is in operable communication with a downstream chamber comprising an immobilized reagent that specifically binds full-length product RNA, wherein the immobilized reagent does not bind less than full-length RNA and double-stranded RNA impurities.

3. The method of claim 1, wherein the support is a microparticle or a bead.

4. The method of claim 1, wherein RNA synthesis is conducted under low salt conditions of 0 to 50 mM.

5. The method of claim 1, wherein RNA synthesis is conducted under high salt conditions of 50 to 1000 mM.

6. The method of claim 1, wherein the reaction mixture further comprises a capture DNA that is 3' end protected, and is complementary to 8 to 20 nucleotides at the 3' end of the product RNA.

7. The method of claim 6, wherein the 3' end of the capture DNA comprises 3' amino, 3'-deoxy (H), 3'-phosphorylation, 3'-O-methyl, 3'-fluorophore, 3'-biotin, 3'-azide, 3'-fluoro, 3'-PEG, or a 3'-mismatched base.

8. The method of claim 1, further comprising purifying the product RNA.

9. The method of claim 6, further comprising removing the capture DNA after product RNA synthesis.

10. A method of synthesizing a product RNA, the method comprising,
- preparing a reaction mixture comprising a functional template DNA for the product RNA, and an RNA polymerase under conditions for RNA synthesis, wherein the functional template DNA and the RNA polymerase are immobilized to a solid support, and wherein the reaction mixture and the solid support are contained in a reaction chamber of a fluidic chip, the fluidic chip comprising fluidic paths for reagent delivery and product RNA removal, and
- synthesizing the product RNA in the reaction mixture and continuously removing the product RNA from the reaction chamber while flowing fresh RNA synthesis reagents into the reaction chamber,
- wherein the RNA polymerase comprises a haloalkane dehalogenase tag, and wherein the functional template DNA is covalently linked to the haloalkane dehalogenase tag of the RNA polymerase via a 3' or 5'halogen-modification.

11. The method of claim 10, wherein the reaction chamber is in operable communication with a downstream chamber comprising an immobilized reagent that specifically binds full-length product RNA, wherein the immobilized reagent does not bind less than full-length RNA and double-stranded RNA impurities.

12. The method of claim 10, wherein the support is a microparticle or a bead.

13. The method of claim 10, wherein RNA synthesis is conducted under low salt conditions of 0 to 50 mM.

14. The method of claim 10, wherein RNA synthesis is conducted under high salt conditions of 50 to 1000 mM.

15. The method of claim 10, wherein the reaction mixture further comprises a capture DNA that is 3' end protected, and is complementary to 8 to 20 nucleotides at the 3' end of the product RNA.

16. The method of claim 15, wherein the 3' end of the capture DNA comprises 3' amino, 3'-deoxy (H), 3'-phosphorylation, 3'-O-methyl, 3'-fluorophore, 3'-biotin, 3'-azide, 3'-fluoro, 3'-PEG, or a 3'-mismatched base.

17. The method of claim 10, further comprising purifying the product RNA.

18. The method of claim 15 further comprising removing the capture DNA after product RNA synthesis.

* * * * *

SEQUENCE LISTING

<160> NUMBER OF SEQ ID NOS: 14

<210> SEQ ID NO 1
<211> LENGTH: 24
<212> TYPE: RNA
<213> ORGANISM: Artificial
<220> FEATURE:
<223> OTHER INFORMATION: Synthetic RNA

<400> SEQUENCE: 1
ggaauaagua gaggugaaga uuua                                        24

<210> SEQ ID NO 2
<211> LENGTH: 32
<212> TYPE: RNA
<213> ORGANISM: Artificial
<220> FEATURE:
<223> OTHER INFORMATION: Self-primed extension of synthetic RNA

<400> SEQUENCE: 2
ggaauaagua gaggugaaga uuuaccucua cu                               32

<210> SEQ ID NO 3
<211> LENGTH: 17
<212> TYPE: DNA
<213> ORGANISM: Artificial
<220> FEATURE:
<223> OTHER INFORMATION: capture DNA

<400> SEQUENCE: 3
taaatcttca cctctac                                                17

```
<210> SEQ ID NO 4
<211> LENGTH: 11
<212> TYPE: DNA
<213> ORGANISM: Artificial
<220> FEATURE:
<223> OTHER INFORMATION: capture DNA

<400> SEQUENCE: 4
taaatcttca c                                                          11

<210> SEQ ID NO 5
<211> LENGTH: 14
<212> TYPE: DNA
<213> ORGANISM: Artificial
<220> FEATURE:
<223> OTHER INFORMATION: capture DNA

<400> SEQUENCE: 5
taaatcttca cctc                                                       14

<210> SEQ ID NO 6
<211> LENGTH: 17
<212> TYPE: DNA
<213> ORGANISM: Artificial
<220> FEATURE:
<223> OTHER INFORMATION: capture DNA

<400> SEQUENCE: 6
taaatgcgtc gacgtag                                                    17

<210> SEQ ID NO 7
<211> LENGTH: 33
<212> TYPE: RNA
<213> ORGANISM: Artificial
<220> FEATURE:
<223> OTHER INFORMATION: Synthetic RNA

<400> SEQUENCE: 7
ggagguacga cucgcacgua gaggugaagu uua                                  33

<210> SEQ ID NO 8
<211> LENGTH: 8
<212> TYPE: PRT
<213> ORGANISM: Artificial
<220> FEATURE:
<223> OTHER INFORMATION: Strep tag-II(R) peptide

<400> SEQUENCE: 8

Trp Ser His Pro Gln Phe Glu Lys
1               5

<210> SEQ ID NO 9
<211> LENGTH: 22
<212> TYPE: DNA
<213> ORGANISM: Artificial
<220> FEATURE:
<223> OTHER INFORMATION: nontemplate strand NT

<400> SEQUENCE: 9
aattaatacg actcactata gg                                              22

<210> SEQ ID NO 10
<211> LENGTH: 26
<212> TYPE: DNA
<213> ORGANISM: Artificial
<220> FEATURE:
```

```
<223> OTHER INFORMATION: nontemplate strand NT-biotin

<400> SEQUENCE: 10
ttttaattaa tacgactcac tatagg                                              26

<210> SEQ ID NO 11
<211> LENGTH: 44
<212> TYPE: DNA
<213> ORGANISM: Artificial
<220> FEATURE:
<223> OTHER INFORMATION: template strand 24

<400> SEQUENCE: 11
taaatcttca cctctactac ctcctatagt gagtcgtatt aatt                          44

<210> SEQ ID NO 12
<211> LENGTH: 54
<212> TYPE: DNA
<213> ORGANISM: Artificial
<220> FEATURE:
<223> OTHER INFORMATION: template strand 24alt

<400> SEQUENCE: 12
taaatcttca cctctacgtg cgagtcgtac ctcctatagt gagtcgtatt aatt               54

<210> SEQ ID NO 13
<211> LENGTH: 54
<212> TYPE: DNA
<213> ORGANISM: Artificial
<220> FEATURE:
<223> OTHER INFORMATION: template strand 34

<400> SEQUENCE: 13
taaatcttca cctctacgtg cgagtcgtac ctcctatagt gagtcgtatt aatt               54

<210> SEQ ID NO 14
<211> LENGTH: 53
<212> TYPE: DNA
<213> ORGANISM: Artificial
<220> FEATURE:
<223> OTHER INFORMATION: template strand 34alt

<400> SEQUENCE: 14
taaatgcgtc gacgtagttt gagtcatacc tcctatagtg agtcgtatta att                53
```